United States Patent
Kataoka et al.

(10) Patent No.: US 9,114,177 B2
(45) Date of Patent: Aug. 25, 2015

(54) BLOCK COPOLYMER HAVING PHENYLBORONIC ACID GROUP INTRODUCED THEREIN, AND USE THEREOF

(71) Applicants: THE UNIVERSITY OF TOKYO, Tokyo (JP); NATIONAL UNIVERSITY CORPORATION TOKYO MEDICAL AND DENTAL UNIVERSITY, Tokyo (JP); NanoCarrier Co., Ltd., Kashiwa-shi (JP)

(72) Inventors: Kazunori Kataoka, Tokyo (JP); Takehiko Ishii, Tokyo (JP); Mitsuru Naito, Tokyo (JP); Akira Matsumoto, Tokyo (JP); Yasuki Kato, Kashiwa (JP)

(73) Assignees: THE UNIVERSITY OF TOKYO, Tokyo (JP); NATIONAL UNIVERSITY CORPORATION TOKYO MEDICAL AND DENTAL UNIVERSITY, Tokyo (JP); NANOCARRIER CO., LTD., Kashiwa (JP)

( * ) Notice: Subject to any disclaimer, the term of this patent is extended or adjusted under 35 U.S.C. 154(b) by 0 days.

(21) Appl. No.: 14/358,816

(22) PCT Filed: Nov. 19, 2012

(86) PCT No.: PCT/JP2012/079897
§ 371 (c)(1),
(2) Date: May 16, 2014

(87) PCT Pub. No.: WO2013/073697
PCT Pub. Date: May 23, 2013

(65) Prior Publication Data
US 2015/0051347 A1 Feb. 19, 2015

Related U.S. Application Data

(60) Provisional application No. 61/561,022, filed on Nov. 17, 2011.

(51) Int. Cl.
*A61K 31/713* (2006.01)
*A61K 47/48* (2006.01)
*C08G 81/00* (2006.01)
*C08G 69/40* (2006.01)
*C08G 69/42* (2006.01)

(52) U.S. Cl.
CPC ......... *A61K 47/48323* (2013.01); *A61K 31/713* (2013.01); *A61K 47/48215* (2013.01); *C08G 69/40* (2013.01); *C08G 69/42* (2013.01); *C08G 81/00* (2013.01); *C08G 2650/28* (2013.01)

(58) Field of Classification Search
CPC .............. A61K 47/48215; A61K 47/48323; A61K 31/713; C08G 69/10; C08G 69/40; C08G 69/42; C08G 81/00; C08G 2650/28
See application file for complete search history.

(56) References Cited

U.S. PATENT DOCUMENTS

| 5,780,454 A | 7/1998 | Adams et al. |
| 2008/0248097 A1 | 10/2008 | Kwon et al. |
| 2010/0040556 A1 | 2/2010 | Davis et al. |
| 2010/0221320 A1 | 9/2010 | Kato et al. |
| 2010/0247669 A1 | 9/2010 | Eliasof et al. |
| 2010/0298495 A1 | 11/2010 | Bobe et al. |
| 2011/0142787 A1 | 6/2011 | Nagasaki et al. |
| 2012/0283403 A1 | 11/2012 | Matsumoto et al. |
| 2014/0017192 A1 | 1/2014 | Saito et al. |

FOREIGN PATENT DOCUMENTS

| JP | H05-301880 A | 11/1993 |
| JP | H08-3172 A | 1/1996 |
| JP | 2002-179683 A | 6/2002 |
| JP | 2011-140537 A | 7/2011 |
| JP | 2011-173960 A | 9/2011 |
| WO | 96/13266 A | 5/1996 |
| WO | 20091133647 A | 11/2009 |
| WO | 2010/019718 A | 2/2010 |
| WO | 2012/133884 A | 10/2012 |

OTHER PUBLICATIONS

English Translation of Amended Claims 1-7 and 10 Filed Under Art. 34 PCT During the International Phase of parent application No. PCT/JP2012/079897.
English translation of International Preliminary Report on Patentability for parent application No. PCT/JP2012/079897.
English translation of International Search Report for parent application No. PCT/JP2012/079897.
F. Nakanowatari et al., "Micelle formation from PEG-p(Lys) block copolymer with phenyl boronic acid moieties", Polymer Preprints, Japan, May 1999, vol. 48, No. 3, p. 572, including English translation thereof.
K. Kataoka, "Cellular specific material and new drug delivery system" Polyfile, Apr. 1993, pp. 27-31, including English translation thereof.
L Zhao et al., "Glucose-sensitive polypeptide micelles for self-regulated insulin release at physiological pH", J. Mater. Chem., 2012, vol. 22, pp. 12319-12328, including English abstract.

(Continued)

*Primary Examiner* — Robert Jones, Jr.
(74) *Attorney, Agent, or Firm* — J-Tek Law PLLC; Jeffrey D. Tekanic; Scott T. Wakeman

(57) ABSTRACT

A block copolymer includes a polyamino acid chain segment and a hydrophilic polymer chain segment. The polyamino acid chain segment includes at least one amino acid residue having a side chain that contains a cationic group and at least one amino acid residue having a side chain that contains a substituted phenylboronic acid group. In the substituted phenylboronic acid group, at least one hydrogen of the phenyl ring is substituted so that the phenylboronic acid group has a pKa of less than 8. Such a block copolymer serves as a carrier that simultaneously imparts stability to a biotechnology-based drug in blood and provides suitable drug-releasing properties of the drug at an affected area.

20 Claims, 4 Drawing Sheets

(56) References Cited

OTHER PUBLICATIONS

M. Naito et al., "Design and physicochemical evaluation of novel polymeric micelle forming reversible covalent bond with ribose for siRNA delivery carrier", Polymer Preprints, Japan, May 2012, vol. 61, No. 1, p. 1642.

Miyata et al: "PEG-based block catiomers possessing DNA anchoring and endosomal escaping functions to form polyplex micelles with improved stability and high transfection efficacy"; Journal of Controlled Release, Elsevier, Amsterdam, NL, vol. 122, No. 3; Sep. 18, 2007, pp. 252-260, XP022336556, ISSN: 0168-3659.

Singhal RP et al: "New ligands for boronate affinity chromatography"; Journal of Chromatography, Elsevier Science Publishers B.V, NL, vol. 543, Jan. 1, 1991, pp. 17-38, XP026514921; ISSN: 0021-9673.

Akira Matsumoto et al., "Glucose-Responsive Polymer Bearing a Novel Phenylborate Derivative as a Glucose-Sensing Moiety Operating at Physiological pH Conditions", Biomacromolecules, vol. 4, No. 5, Aug. 19, 2003, pp. 1410-1416, XP055105744, ISSN: 1525-7797.

Extended European Search Report from the European Patent Office dated May 11, 2015 in counterpart European patent application No. 12850688.8, including European Search Opinion, Supplementary European Search Report and examined claims 1-7 and 10.

BLOCK COPOLYMER HAVING PHENYLBORONIC ACID GROUP INTRODUCED THEREIN, AND USE THEREOF

CROSS-REFERENCE

This application is the U.S. national stage of International Patent Application No. PCT/JP2012/079897 filed on Nov. 19, 2012, which claims priority to U.S. Provisional Patent Application No. 61/561,022 filed on Nov. 17, 2011.

REFERENCE TO SEQUENCE LISTING FILED VIA EFS-WEB

The present application contains a Sequence Listing that has been electronically submitted in ASCII text format via EFS-Web and is incorporated herein by reference in its entirety. The sequence listing is identified on the electronically-filed text file as follows:

| File Name | Date of Creation | Size (KB) |
|---|---|---|
| NCC006_seq_list.txt | May 15, 2014 | 2 |

TECHNICAL FIELD

The present invention relates to a block copolymer that has (a) phenylboronic acid group (s) introduced therein, and to a complex that includes the block copolymer and a drug.

BACKGROUND ART

Biological pharmaceuticals that utilize a biopolymer such as a protein or a nucleic acid are easily degraded by enzymes or eliminated by the immune system as compared to conventional pharmaceuticals that utilize low-molecular-weight compounds. From the viewpoint of improving delivery of such biotechnology-based drugs to an affected area, the present inventors have developed a drug delivery system (DDS) that uses a polyamino acid-based block copolymer. An aim of the development is to provide a carrier that simultaneously achieves stability in blood (retention properties of the biotechnology-based drugs) and drug-releasing properties at an affected area.

In addition, for a different purpose than DDS development, the present inventors have also advanced fundamental research of biocompatible materials applicable to saccharide sensors and saccharide-responsive actuators. For example, phenylboronic acid-based compounds having a fluorinated phenyl ring have been developed as biocompatible materials (Patent Literature 1).

It should be noted that Patent Literature 2 is prior art concerning a reagent that is obtained by binding a nucleic acid to a polyamino acid-based derivative that uses a phenylboronic acid group and is applied to analyses of behaviors and structures of nucleic acids and nucleic acid-related substances.

CITATION LIST

Patent Literature

[Patent Literature 1] JP 2011-140537 A
[Patent Literature 2] JP 2002-179683 A

SUMMARY OF THE INVENTION

In one aspect of the present teachings, a carrier is disclosed that simultaneously achieves stability of a biotechnology-based drug in blood and drug-releasing properties of the drug at an affected area. It should be noted that, in Patent Literature 2, a reagent carrying a nucleic acid-related substance is disclosed as a DDS. However, this DDS is merely a prodrug like an RNA mimic and easily forms precipitates. The technology described in Patent Literature 2 is intended to provide a DDS different from the DDS developed by the present inventors, and cannot be easily applied as a carrier that exhibits suitable stability in blood.

The present inventors have found that a biocompatible material, which had been created for a purpose different than for the development of a DDS, can significantly improve the stability in blood of a biotechnology-based drug by using a polyamino acid-based block copolymer. That is, according to one aspect of the present teachings, a block copolymer includes a polyamino acid chain segment and a hydrophilic polymer chain segment, the polyamino acid chain segment including at least one amino acid residue having a cationic group in a side chain and at least one amino acid residue having a substituted phenylboronic acid group in a side chain, and the substituted phenylboronic acid group(s) (each) having a phenyl ring in which at least one hydrogen atom thereof is substituted so that the substituted phenylboronic acid group has a pKa of approximately physiological pH.

According to another aspect of the present invention, there is provided a complex. The complex is a complex that includes the block copolymer and a biopolymer.

EFFECTS OF THE INVENTION

According to the present invention, a carrier is provided that simultaneously achieves stability of a biotechnology-based drug in blood and releasing properties of the drug in a target cell.

MODE(S) FOR CARRYING OUT THE INVENTION

[A. Block Copolymer]

Figure 1:
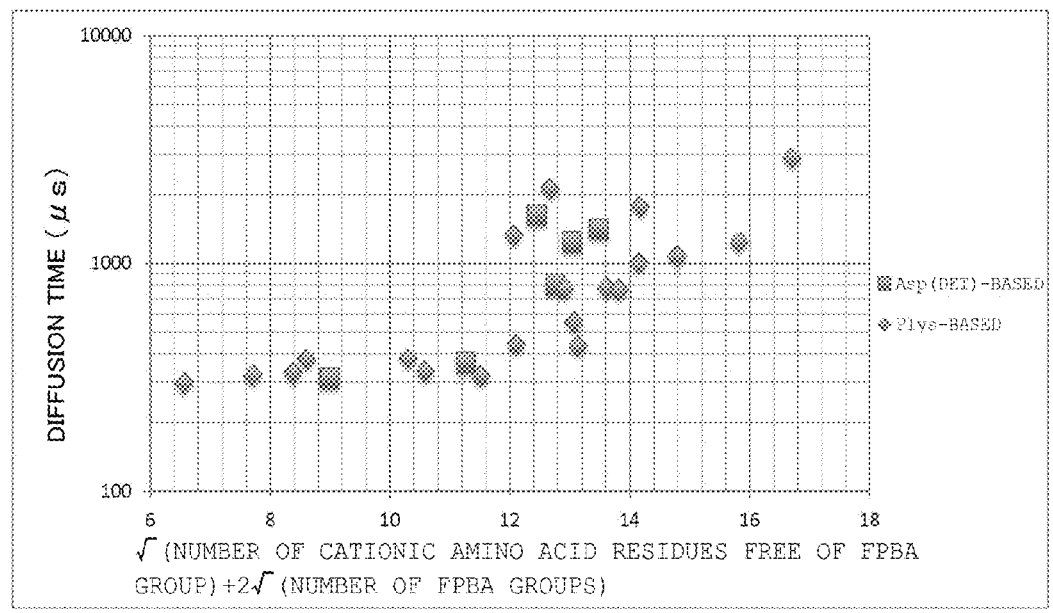
FIG. 1 is a graph showing a relationship between FPBA group contents and complex stability.

A block copolymer of the present invention includes a polyamino acid chain segment and a hydrophilic polymer chain segment. The polyamino acid chain segment includes (an) amino acid residue (s) having a cationic group in a side chain (hereinafter sometimes referred to as "cationic amino acid residue") and (an) amino acid residue (s) having a substituted phenylboronic acid group (hereinafter sometimes referred to as "substituted PBA group") in a side chain, the substituted phenylboronic acid group (s) having a phenyl ring in which at least one hydrogen atom thereof is substituted so as to have a pKa of approximately physiological pH (hereinafter sometimes referred to as "substituted PBA group-containing amino acid residue"). In this context, the cationic amino acid residue and the substituted PBA group-containing amino acid residue may be the same amino acid residue or different amino acid residues. Specifically, the polyamino acid chain segment may include (a) cationic amino acid residue (s) that is (are) free of the substituted PBA group in a side chain and (a) substituted PBA group-containing amino acid residue (s) that is (are) free of the cationic group in a side chain. Alternatively, instead of one or both of the amino acid residues or in addition to the amino acid residues, the polyamino acid chain segment may include an amino acid residue having both the cationic group and the substituted PBA group in a side chain.

From the viewpoint of compatibility with an in vivo environment as typified by blood (less than pH 7.5), in the substituted PBA group, at least one hydrogen atom of the phenyl ring constituting the phenylboronic acid group is substituted with any substituent so that the substituted phenylboronic acid group has a pKa of approximately physiological pH. The pKa of the substituted PBA group is preferably less than 8, more preferably less than 7.5. The number of substituted hydrogen atoms is 1, 2, 3, or 4. When only one hydrogen atom is substituted, the attachment positions of the substituent and $B(OH)_2$ may be at any one of ortho, meta, and para. Examples of the substituent include halogens such as fluorine, chlorine, or bromine; and a nitro group. Of those, from the viewpoint of enhancing the hydrophilicity of the block copolymer and from the viewpoint of adjusting the pKa to less than 7.5, the substituted PBA group is preferably a fluorinated phenylboronic acid group represented by the following formula (I) (hereinafter sometimes referred to as a "FPBA group"). The pKa of the substituted PBA group is specified from a substituted PBA group-containing amino acid synthesized as a monomer. The lower limit of the pKa of the substituted PBA group is not particularly limited, and for example may be 2 or 3.

[Chem. 1]

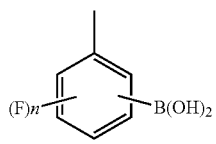

(I)

(In formula (I): F('s) is (are) present independently; n is 1, 2, 3, or 4; and when n is 1, the attachment positions of F and $B(OH)_2$ may be at any one of ortho, meta, and para.)

The block copolymer of the present invention has (a) cationic group (s) in (a) side chain moiety (moieties) of the polyamino acid chain segment, and hence can associate with a biopolymer to form a complex, for example, a polyion complex (PIC).

In addition, the block copolymer of the present invention has the substituted PBA group (s) in (a) side chain moiety (moieties) of the polyamino acid chain segment, and hence may exhibit the following effects. First, the hydrophobicity of the polyamino acid chain segment is enhanced, and hence hydrophobic interactions as well as electrostatic interactions suitably act between a plurality of block copolymers of the present invention in an aqueous medium. As a result, the association force among the polymers is enhanced, and hence block copolymers of the present invention may form a very stable polymer micelle in an aqueous medium. It should be noted that the block copolymers of the present invention in the polymer micelle are surmised to be arranged in a radial fashion so that the polyamino acid chain segments face the inside, and the hydrophilic polymer chain segments face the outside. Examples of the aqueous medium include water, physiological saline, aqueous buffers such as a phosphate buffer, a carbonate buffer, a borate buffer, and an acetate buffer.

Second, in an aqueous medium phenylboronic acid compounds have a reversible covalent binding ability for molecules having a 1,2-diol (cis-diol) or a 1,3-diol. Therefore, the block copolymer of the present invention can be bound strongly to a biopolymer having a 1,2-diol or the like (for example, siRNA) in an aqueous medium via (a) covalent bond(s) to the substituted PBA group(s) as well as by (an) electrostatic bond(s) with the cationic group(s), resulting in the formation of a stable complex (for example, a polymer micelle including the biopolymer encapsulated therein). In particular, the block copolymer of the present invention can be bound to siRNA having cis-diols in the 3'-terminal ribose of both double strands at the two 3'-terminals, and hence may form a very stable complex.

Third, phenylboronic acid usually has a pKa of about 8 to 9; because it has the maximum covalent binding ability for molecules having a 1,2-diol or the like at a pH around the pKa, it has been considered that use of phenylboronic acid would be difficult in principle in an in vivo environment of less than pH 7.5. However, because (a) hydrogen atom(s) of the phenyl ring is (are) substituted so as to have a pKa of approximately physiological pH (preferably exhibits a pKa of less than 8, more preferably a pKa of less than 7.5), the substituted PBA group (s) introduced into the block copolymer of the present invention can suitably exhibit the binding ability in an in vivo environment.

Fourth, because the substituted PBA group is highly hydrophobized in a pH environment equal to or less than the pKa, by appropriately controlling the pKa, it is possible to enhance both the binding to molecules having a 1,2-diol or the like and the hydrophobic interactions among the block copolymers in an in vivo environment. As a result, a very stable complex formed by the molecules can be obtained.

[A-1. Polyamino Acid Chain Segment]

The polyamino acid chain segment includes (a) cationic amino acid residue(s) having a cationic group in a side chain and (a) substituted PBA group-containing amino acid residue(s) having a substituted PBA group in a side chain.

The cationic amino acid residue(s) is (are) preferably (a) cationic amino acid residue(s) having an amino group in a side chain. By having the amino group(s) in the side chain, the amino group(s) can coordinate with the boron(s) of the substituted PBA group(s) in an aqueous medium. As a result, hydrophobization of the block copolymer due to introduction of the substituted PBA group(s) can be avoided to maintain high hydrophilicity. It should be noted that even in a state where the amino group (s) coordinate (s) with boron(s), the binding ability of the substituted PBA group(s) for molecule(s) having a cis-diol or the like can be maintained.

As amino acids from which the cationic amino acid residue(s) having an amino group in a side chain is (are) derived, for example, basic amino acids such as lysine, ornithine, arginine, homoarginine, or histidine, as well as amino acid derivatives obtained by introducing any appropriate amine compound into an acidic amino acid, are mentioned.

Of those, preferred are lysine and amino acid derivatives obtained by substituting the —OH moiety of a carboxyl group (—C(=O)OH) of the acidic amino acid with any one of the groups of the following formulas (i) to (iv); more preferred are lysine and amino acid derivatives obtained by substituting the —OH moiety of a carboxyl group (—O(=O)OH) at the α-position or β-position of aspartic acid or at the α-position or γ-position of glutamic acid with any one of the groups of the following formulas (i) to (iv); and still more preferred are lysine and amino acid derivatives obtained by substituting the —OH moiety of a carboxyl group (—C(=O)OH) at the α-position or β-position of aspartic acid or at the α-position or γ-position of glutamic acid with the group of the following formula (i):

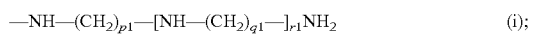  (i);

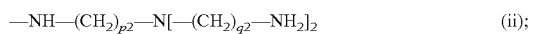  (ii);

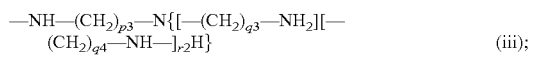  (iii);

and

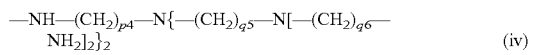  (iv)

in formulas (i) to (iv): p1 to p4, q1 to q6, and r1 and r2 are each independently an integer of 1 to 5.

In formulas (i) to (iv), p1 to p4 and q1 to q6 are each independently preferably 2 or 3, more preferably 2. In addition, r1 and r2 are each independently preferably an integer of 1 to 3.

In case the cationic amino acid residue(s) is (are) (a) lysine residue(s), there are advantages in that the polyamino acid chain is easily synthesized and the resultant block copolymer excels exceedingly in biocompatibility. In addition, it has been demonstrated that, incase the cationic amino acid residue (s) is (are) (an) amino acid residue(s) obtained by substituting the —OH moiety of a carboxyl group (—C(=O)OH) of the acidic amino acid with any one of the groups of the formulas (i) to (iv), because the residues have a plurality of different amine functional groups, they exhibit a plurality of stages of pKa's, a plurality of amine functional groups are partially protonated under physiological conditions at pH 7.4 and damage to cells is low. In addition, there is an advantage in that interactions with nucleic acids or the like enable suitable formation of a complex such as a PIC. Further, when the thus-formed complex is internalized into an endosome (pH 5.5), the protonation of the polyamino acid chain segment further proceeds due to the decrease of the environmental pH, and endosomal escape may be promoted based on a buffer effect (or a proton sponge effect) or enhanced membrane-damaging activity. As a result, it is possible to improve the efficiency of the drug delivery to the cytoplasm.

The substituted PBA group is typically introduced into the side chain of the substituted PBA group-containing amino acid residue via a divalent linking group. Examples of the divalent linking group include an amide bond, a carbamoyl bond, an alkyl bond, an ether bond, an ester bond, a thioester bond, a thioether bond, a sulfonamide bond, a urethane bond, a sulfonyl bond, a thymine bond, a urea bond, and a thiourea bond.

As amino acid residues into which the substituted PBA group introduced, any appropriate amino acid residue may be selected as long as the substituted PBA group is introduced via the linking group. From the viewpoint of ease of synthesis, the substituted PBA group is preferably introduced into a cationic amino acid residue having an amino group in the side chain. Specifically, the substituted PBA group may be introduced into a cationic amino acid residue having an amino group in the side chain via an amide bond formed by reaction of the amino group with carboxyphenylboronic acid, in which at least one hydrogen atom of a phenyl ring has been substituted, or an ester thereof. In this context, only one substituted PBA group or a plurality of substituted PBA groups may be introduced into a cationic amino acid residue having a plurality of amino groups in a side chain. In case only one substituted PBA group is introduced, the substituted PBA group-containing amino acid residue after the introduction has both the amino group and the substituted PBA group in the side chain, and hence is also a cationic amino acid residue. Therefore, in the present invention, a polyamino acid chain segment containing only such amino acid residues is also understood to include both the cationic amino acid residue and the substituted PBA group-containing amino acid residue. However, in determining the sum of the number of cationic amino acid residues and the number of substituted PBA group-containing amino acid residues in the polyamino acid chain segment containing such amino acid residues, such amino acid residues are counted as any one of the cationic amino acid residues and the substituted PBA group-containing amino acid residues.

The polyamino acid chain segment may further include (an) amino acid residue(s) having a hydrophobic group in a side chain (hereinafter sometimes referred to as a "hydrophobic amino acid residue") as well as the cationic amino acid residue(s) and the substituted PBA group-containing amino acid residue (s). By including the hydrophobic amino acid residue (s), in an aqueous medium hydrophobic interactions among the block copolymers of the present invention increase. As a result, a more stable polymer micelle may be formed. In addition, the hydrophobic amino acid residue(s) stick(s) into hydrophobic moieties on the cell membrane and can function as an anchor for fixing the polymer micelle to the cell membrane. Therefore, in case a biopolymer such as a nucleic acid is encapsulated in the polymer micelle, the internalization rate of the biopolymer into cells can be increased.

Amino acids from which the hydrophobic amino acid residue (s) is (are) derived are preferably exemplified by amino acids having a solubility of 5 g or less in 100 g of water at 25° C., more preferably 4 g or less. Examples of such amino acids include non-polar natural amino acids such as leucine, isoleucine, phenylalanine, methionine, or tryptophan, and hydrophobic derivatives of amino acids that have a hydrophobic group introduced into a side chain. A preferred example of the hydrophobic derivative of the amino acid is a derivative that has a hydrophobic group introduced into a side chain of an acidic amino acid such as aspartic acid or glutamic acid.

The hydrophobic group (s) to be introduced preferably may be exemplified by saturated or unsaturated linear or branched aliphatic hydrocarbon groups having 6 to 27 carbon atoms, aromatic hydrocarbon groups having 6 to 27 carbon atoms, or steryl groups.

Saturated linear or branched aliphatic hydrocarbon groups having 6 to 27 carbon atoms are exemplified by a pentacosyl group, a hexacosyl group, or a heptacosyl group as well as alkyl groups having 6 to 27 carbon atoms.

Examples of unsaturated linear or branched aliphatic hydrocarbon groups having 6 to 27 carbon atoms are groups in which 1 to 5 carbon-carbon single bonds in a chain of the alkyl group having 6 to 27 carbon atoms are replaced by carbon-carbon double bonds. As unsaturated fatty acids having such groups, for example, lauric acid (or dodecanoic acid), myristic acid (or tetradecanoic acid), palmitic acid (or hexadecanoic acid), palmitoleic acid (or 9-hexadecenoic acid), stearic acid (or octadecanoic acid), oleic acid, linoleic acid, linolenic acid, eleostearic acid (or 9,11,13-octadecatrienoic acid), arachidic acid, arachidonic acid, behenic acid, lignoceric acid, nervonic acid, cerotic acid, and montanic acid are mentioned.

Examples of aromatic hydrocarbon groups having 6 to 27 carbon atoms include an aryl group and an aralkyl group. Preferred specific examples of those groups include a phenyl group, a naphthyl group, a tolyl group, a xylyl group, a benzyl group, and a phenethyl group.

Sterols from which the steryl group are derived mean natural, semisynthetic, or synthetic compounds based on a cyclopentanone hydrophenanthrene ring ($C_{17}H_{28}$) and derivatives thereof. For example, natural sterols are exemplified by, but not limited to, cholesterol, cholestanol, dihydrocholesterol, cholic acid, campesterol, or sitosterol. Semisynthetic or synthetic compounds thereof may be, for example, synthetic precursors of those natural products (as necessary, encompassing compounds in which part or all of, if present, certain functional groups, hydroxy groups have been protected with a hydroxy protective group known in the art, or compounds in which a carboxyl group has been protected with a carboxyl protective group). Further, sterol derivatives mean that, for example, without adversely affecting the object of the present invention, a $C_{1-12}$ alkyl group, a halogen atom such as chlorine, bromine, or fluorine may be introduced into the cyclopentanone hydrophenanthrene ring, and the ring system may be saturated or partially unsaturated. Sterols from which the steryl group is derived are preferably a sterol originating from an animal or vegetable oil such as cholesterol, cholestanol, dihydrocholesterol, cholic acid, campesterol, or sitosterol, more preferably cholesterol, cholestanol, or dihydrocholesterol, particularly preferably cholesterol.

The polyamino acid chain segment may include, as each of the cationic amino acid residue(s), the substituted PBA group-containing amino acid residue (s), and the hydrophobic amino acid residue(s), one type of amino acid residue or two or more types of amino acid residues. In addition, the binding order of the cationic amino acid residue(s), substituted PBA group-containing amino acid residue(s), and hydrophobic amino acid residue(s) in the polyamino acid chain segment is arbitrary, and it may be a random structure or a block structure.

The number of cationic amino acid residue (s), substituted PBA group-containing amino acid residue (s), and hydrophobic amino acid residue(s) contained in the polyamino acid chain segment may be appropriately adjusted depending on the type of each of the amino acid residues, the application of the block copolymer, or the like. From the viewpoint of improving retention properties (stability in blood) of the biopolymer with additional certainty, the number of each of the amino acid residues is preferably adjusted so that the following relationship expression is satisfied. It should be noted that, in case a plurality of cationic groups are present in a repeating unit (amino acid residue) constituting the polyamino acid chain segment, a plurality of substituted PBA groups may be introduced into one repeating unit. Therefore, the total number of substituted PBA groups in the polyamino acid chain segment may exceed the sum of the number of cationic amino acid residues that have no substituted PBA group introduced and the number of amino acid residues that have the substituted PBA group introduced (substituted PBA group-containing amino acid residue). In addition, in an analysis using a general-purpose structural analysis device, it may be difficult to distinguish whether a plurality of the substituted PBA groups have been introduced into one repeating unit or separately introduced into a plurality of repeating units. Therefore, in the relationship expression, for the sake of convenience, the number of cationic amino acid residue(s) that is (are) free of the substituted PBA group may be defined as a value determined by subtracting the number of substituted PBA group(s) (measured value) from the sum of the number of cationic amino acid residue(s) and the number of substituted PBA group-containing amino acid residue (s) (theoretical value) (however, the lower limit is defined as 0). It should be noted that the upper limit of the following relationship expression is not particularly limited, and may be, for example, 40, 38, 35, or 25. When the value of the following relationship expression is 14 or more, or 15 or more, the stability in blood is improved with more certainty.

$$\sqrt{\begin{array}{c}\text{Number of cationic amino acid} \\ \text{residues free of substituted} \\ \text{phenylboronic acid group in} \\ \text{polyamino acid chain segment}\end{array}} + \qquad \text{[No. 1]}$$

$$2\sqrt{\begin{array}{c}\text{Number of substituted} \\ \text{phenylboronic acid groups in} \\ \text{polyamino acid chain segment}\end{array}} \geq 12.0$$

[A-2. Hydrophilic Polymer Chain Segment]

The hydrophilic polymer chain segment may be formed of any appropriate hydrophilic polymer. Examples of the hydrophilic polymer include poly(ethylene glycol), polysaccharide, poly(vinylpyrrolidone), poly(vinyl alcohol), poly(acrylamide), poly(acrylic acid), poly(methacrylamide), poly (methacrylic acid), poly(methacrylic acid ester), poly(acrylic acid ester), polyamino acid, poly(malic acid), and derivatives thereof. Specific examples of the polysaccharide include starch, dextran, fructan, and galactan. Of those, poly(ethylene glycol) may be preferably used because terminal-reactive polyethylene glycols having a variety of functional groups at their terminus are commercially available, polyethylene glycols having a variety of molecular weights are commercially available, and these polyethylene glycols are readily available.

[A-3. Specific Examples of the Block Copolymer]

Specific examples of block copolymers in particularly preferred embodiments of the present invention are represented by formulas (1) to (4). In the block copolymers of formulas (1) to (4), the substituted PBA group (s) is (are) introduced into (a) side chain (s) of (a) cationic amino acid residue (s).

[Chem. 2]

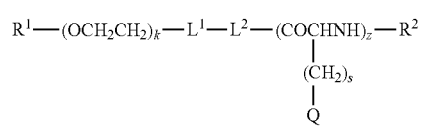

(1)

[Chem. 3]

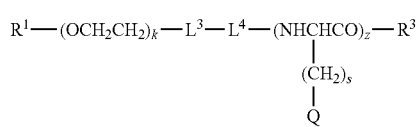

(2)

[Chem. 4]

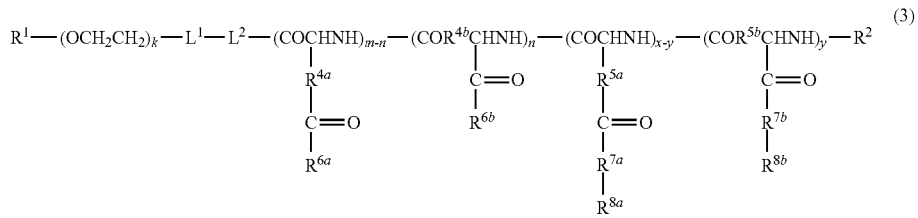

(3)

[Chem. 5]

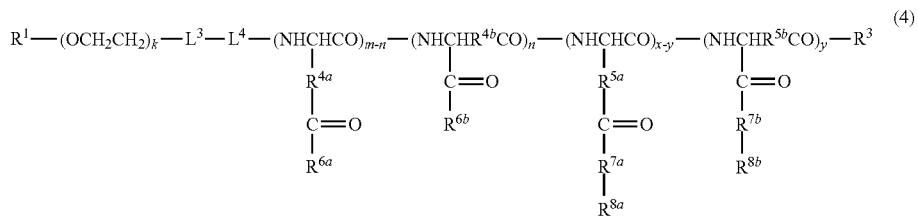

(4)

(In formulas (1) to (4):

the $R^1$ group is a hydrogen atom or an unsubstituted or substituted linear or branched alkyl group having 1 to 12 carbon atoms;

the $R^2$ group is a hydrogen atom, an unsubstituted or substituted linear or branched alkyl group having 1 to 12 carbon atoms, or an unsubstituted or substituted linear or branched alkylcarbonyl group having 1 to 24 carbon atoms;

the $R^3$ group is a hydroxyl group, an unsubstituted or substituted linear or branched alkyloxy group having 1 to 12 carbon atoms, an unsubstituted or substituted linear or branched alkenyloxy group having 2 to 12 carbon atoms, an unsubstituted or substituted linear or branched alkynyloxy group having 2 to 12 carbon atoms, or an unsubstituted or substituted linear or branched alkyl-substituted imino group having 1 to 12 carbon atoms;

the $R^{4a}$, $R^{4b}$, $R^{5a}$, and $R^{5b}$ groups are each independently a methylene group or an ethylene group;

the $R^{6a}$ and $R^{6b}$ groups are each independently a group selected from the groups of the above-described formulas (i) to (iv);

the $R^{7a}$ and $R^{7b}$ groups are each independently —O— or —NH—;

the $R^{8a}$ and $R^{8b}$ groups are each independently a saturated or unsaturated linear or branched aliphatic hydrocarbon group having 6 to 27 carbon atoms, an aromatic hydrocarbon group having 6 to 27 carbon atoms, or a steryl group;

the Q group is —$NH_2$, —NHC(=NH) $NH_2$, or a group represented by the following formula (II),

[Chem. 6]

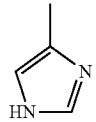

(II)

$L^1$ and $L^3$ are each independently —S—S— or a valence bond;

$L^2$ is —NH—, —O—, —O($CH_2$)$_{p1}$—NH—, or -$L^{2a}$-($CH_2$)$_{q1}$-$L^{2b}$-, where p1 and q1 are each independently an integer of 1 to 5, $L^{2a}$ is OCO, OCONH, NHCO, NHCOO, NHCONH, CONH, or COO, and $L^{2b}$ is NH or O;

$L^4$ is —OCO—($CH_2$)$_{p2}$—CO—, —NHCO—($CH_2$)$_{p3}$—CO—, or -$L^{4a}$-($CH_2$)$_{q2}$—CO—, where p2, p3, and q2 are each independently an integer of 1 to 5, $L^{4a}$ is OCONH, —$CH_2$NHCO—, NHCOO, NHCONH, CONH, or COO;

k is an integer of 30 to 20,000;
s is an integer of 1 to 6;
m is an integer of 1 to 300;
n is an integer of 0 to m;
x is an integer of 0 to 80;
y is an integer of 0 to x;
z is an integer of 2 to 300;

with the proviso that, when the total number of primary amino groups and secondary amino groups included in z of group Q, or the total number of primary amino groups and secondary amino groups included in (m-n) of the $R^{6a}$ group and n of the $R^{6b}$ group, is defined as w, 1 or more but less than w of hydrogen atom(s) of the amino group(s) is (are) substituted with (an) acyl group(s) having a substituted PBA group (for example, an FPBA group represented by formula (I)).)

In formulas (1) to (4), both of $L^1$ and $L^2$ and both of $L^3$ and $L^4$ each need to be combined together so as to form one linking group. For example, in case $L^2$ is —NH—, $L^1$ is not —S—S— but rather is a valence bond.

In formulas (1) to (4), k, which represents the number of repetitions of ethylene glycol (or oxyethylene), is an integer of 30 to 20,000, preferably 40 to 2,000, more preferably 50 to 1,500.

An alkyl moiety in the linear or branched alkyloxy group, alkyl-substituted imino group, and alkyl group having 1 to 12 carbon atoms, which are defined by the $R^1$ to $R^3$ groups, may be, for example, a methyl group, an ethyl group, an n-propyl group, an isopropyl group, an n-butyl group, an sec-butyl group, a tert-butyl group, an n-hexyl group, a decyl group, and an undecyl group. An alkenyl or alkynyl moiety in the linear or branched alkenyloxy group having 2 to 12 carbon atoms or the linear or branched alkynyloxy group having 2 to 12 carbon atoms may be exemplified by an alkenyl or alkynyl moiety containing a double bond or a triple bond in the alkyl group having 2 or more carbon atoms as exemplified above.

For such groups or moieties, substituents in a "substituted" case may be exemplified by, but not limited to, a $C_{1-6}$ alkoxy group, an aryloxy group, an aryl $C_{1-3}$ oxy group, a cyano group, a carboxyl group, an amino group, a $C_{1-6}$ alkoxycarbonyl group, a $C_{2-7}$ acylamide group, a tri-$C_{1-6}$ alkyl siloxy group, a siloxy group, or a silylamino group, or may be exemplified by an acetalized formyl group, a formyl group, or a halogen atom such as chlorine or fluorine. In this context, for example, the expression "$C_{1-6}$" means 1 to 6 carbon atoms and is used with the same meaning in the following description. In addition, an unsubstituted or substituted linear or branched alkyl moiety having 1 to 12 carbon atoms in the unsubstituted or substituted linear or branched alkylcarbonyl group having 1 to 24 carbon atoms may be selected with reference to the above-described examples, and an alkyl moiety having 13 or more carbon atoms may be, for example, a tridecyl group, a tetradecyl group, a pentadecyl group, a nonadecyl group, a docosanyl group, or a tetracosyl group.

In another embodiment, a substituent for the $R^1$ group may be a group containing a target binding site. The introduction of the target binding site into the terminus of a polymer can improve drug (biopolymer) delivery to a desired target site. The group containing the target binding site may be any appropriate group as long as the group has targeting properties or functionality for a tissue to be targeted; for example, the group may be a group originating from a physiologically-active substance such as an antibody or a fragment thereof, or another protein having functionality or targeting properties, a peptide, an aptamer, a sugar such as lactose, or folic acid, and derivatives thereof.

An example of the $R^1$ group substituted by a group including the target binding site is represented by the following formula (III):

[Chem. 7]

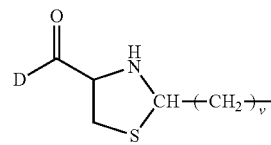

(III)

where: v represents an integer of 1 to 5, and D represents the target binding site.

D is preferably a peptide having a weight average molecular weight of 50 to 20,000, more preferably a peptide having a weight average molecular weight of 100 to 10,000, still more preferably a peptide having a weight average molecular weight of 150 to 3,000.

Further, D is preferably a peptide having 1 to 200 amino acid residues, more preferably a peptide having 1 to 100 amino acid residues, still more preferably a peptide having 1 to 30 amino acid residues.

Examples of the peptide include peptides capable of specifically binding to integrin, which is involved in angiogenesis, intimal thickening, and malignant tumor growth, and specific examples thereof include RGD peptides. By using an RGD peptide as the target binding site, particles, which are capable of specifically recognizing a diseased portion, and pharmaceutical compositions using the particles are obtainable. The RGD peptides as used herein refer to peptides that include an arginine-glycine-aspartic acid (RGD) sequence. The RGD peptide is preferably a cyclic RGD (cRGD) peptide. Specifically, D may be represented by the following formula (IV):

[Chem. 8]

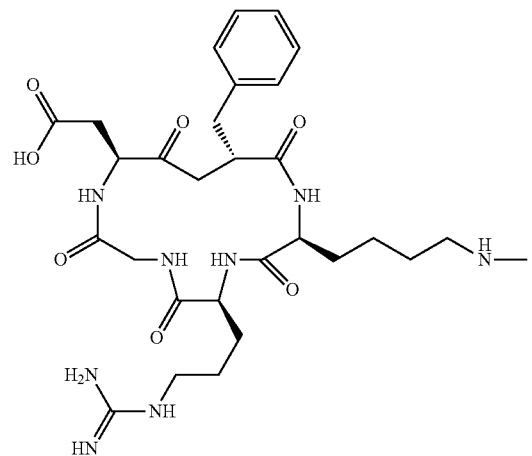

(IV)

In formulas (1) to (4), the groups of formulas (i) to (iv) defined in the $R^{6a}$ and $R^{6b}$ groups and the hydrocarbon group or steryl group defined in the $R^{8a}$ and $R^{8b}$ groups are as mentioned above. For the Q, $R^{6a}$, $R^{6b}$, $R^{8a}$, and $R^{8b}$ groups, the same group may be selected for all of repeating units belonging thereto, or different groups may be selected. Further, s is, for example, 1, 3, or 4.

In formula (3) or (4), in case both of the $R^{4a}$ and $R^{4b}$ groups represent an ethylene group, typically polyamino acids are represented in which n represents the integer 0 or in which m-n represents the integer 0. The former represents, for example, poly-α-glutamic acid, which is obtained by the polymerization of an N-carboxylic anhydride of glutamic acid γ-benzyl ester, and the latter represents, for example, poly-γ-glutamic acid, which strains of the bacteria genus *Bacillus*, such as *Bacillus subtilis natto*, produce. On the other hand, in case both of the $R^{4a}$ and $R^{4b}$ groups represent a methylene group, it is understood that the respective repeating units having those groups may coexist with each other. The same holds true for the $R^{5a}$ and $R^{5b}$ groups. From the viewpoint of manufacturing efficiency, it is preferred that the $R^{4a}$ and $R^{4b}$ groups are methylene groups and the $R^{5a}$ and $R^{5b}$ groups are ethylene groups.

From the viewpoint of the stability of the polymer micelle that will be formed, the total number z of cationic amino acid residues and substituted PBA group-containing amino acid residues included in the block copolymer of formula (1) or (2) is an integer of 1 to 300, preferably 20 to 300, more preferably 30 to 200, still more preferably 40 to 150.

From the viewpoint of the stability of the polymer micelle that will be formed, the total number m of cationic amino acid residues and substituted PBA group-containing amino acid residues included in the block copolymer of formula (3) or (4) is an integer of 1 to 300, preferably 1 to 200, more preferably 1 to 150. In case the block copolymer includes (a) hydrophobic amino acid residue (s) (that is, in case x is not 0), the number of cationic amino acid residue (s) may be, for example, an integer of 1 to 20, preferably 1 to 15, more preferably 1 to 10, still more preferably 1 to 5. According to such block copolymers, the release of the biopolymer as typified by nucleic acid can take place more suitably.

The number x of hydrophobic amino acid residue(s) that may be included in the block copolymer of formula (3) or (4) may be appropriately adjusted depending on the type or number of cationic amino acid residue(s), the application of the block copolymer, or the like. The number x of hydrophobic amino acid residues is an integer of preferably 1 to 80, more preferably 5 to 70, still more preferably 10 to 60.

In the block copolymers of formulas (1) to (4), the number of substituted PBA group-containing amino acid residues may be appropriately adjusted depending on the type or number of cationic amino acid residue (s), the application of the block copolymer, or the like. In the block copolymers, in particular, in the block copolymers of formulas (1) and (2), the substituted PBA group (s) is (are) preferably introduced into the side chain (s) of the cationic amino acid residue (s) so that the following relationship is satisfied. When such relationship is satisfied, the retention properties (stability in blood) of the biopolymer due to the block copolymer are improved with more certainty. It should be noted that the upper limit of the following relationship expression is not particularly limited, and may be 40, 38, 35, or 25, for example. When the value of the following relationship expression is 14 or more, or 15 or more, the stability in blood is improved with more certainty.

$$2\sqrt{\dfrac{\text{Number of cationic amino acid residues free of substituted phenylboronic acid group in polyamino acid chain segment} + \text{Number of substituted phenylboronic acid groups in polyamino acid chain segment}}} \geq 12.0 \quad [\text{No. 2}]$$

[A-4. Block Copolymer Preparation Method]

Block copolymers of the present invention can be prepared by any appropriate synthesis method. An example of the synthesis method for a block copolymer in a preferred embodiment of the present invention is as follows. That is, the block copolymer can be prepared by: forming a polyethylene glycol chain by anion living polymerization using an initiator capable of providing $R^1$; introducing an amino group at the growing end side of the polyethylene glycol chain; from the amino end, polymerizing a protected amino acid derivative such as NCA-Lys (TFA) to form a polyamino acid chain segment; deprotecting the side chains of the polyamino acids to expose the amino groups; and subjecting the exposed amino groups to a reaction with the carboxyl group of a fluorinated carboxyphenylboronic acid to introduce a desired number of FPBA groups into the side chain(s) via amide bond(s).

A block copolymer in another preferred embodiment of the present invention may be prepared, for example, as follows. That is, the block copolymer can be prepared by: forming a polyethylene glycol chain by anion living polymerization using an initiator capable of providing $R^1$; introducing an amino group at the growing end side of the polyethylene glycol chain; from the amino end, polymerizing an N-carboxylic anhydride of a protected amino acid such as β-benzyl-L-aspartate or γ-benzyl-L-glutamate to form a polyamino acid chain segment; subsequently subjecting the polyamino acid to a reaction with an amine compound such as diethylenetriamine (DET) to introduce (an) amine residue(s) such as a DET group into the amino acid side chain(s) by an ester-amide exchange reaction; and subsequently subjecting amino groups of the amine residues to a reaction with the carboxyl group of a fluorinated carboxyphenylboronic acid to introduce a desired number of FPBA groups into the side chain via (an) amide bond(s). In this case, if the polyamino acid chain segment is formed by combining β-benzyl-L-aspartate and γ-benzyl-L-glutamate, the subsequent ester-amide exchange reaction occurs preferentially for β-benzyl-L-aspartate. As a result, a block copolymer may be obtained that includes (an) amino acid residue(s) originating from γ-benzyl-L-glutamate as the hydrophobic amino acid residue(s).

It should be noted that a portion of the amino acid ester residues may undergo a structural change by nucleophilic attack of an amine (for example, imide ring formation through the dealcoholization of an amino acid ester residue) during the synthesis process. In the present invention, the polyamino acid chain segment may further include residues that have undergone such structural change. In this case, the residues that have undergone the structural change are excluded from the cationic amino acid residue, the substituted PBA group-containing amino acid residue, and the hydrophobic amino acid residue. Further, a portion of the NH groups and $NH_2$ groups in the cationic amino acid residues may be converted into (a) salt(s) (mainly hydrochloride) by use of an acid (mainly hydrochloric acid) during the synthesis process. In the present invention, the polyamino acid chain segment may include such structure. In other words, a portion of the NH groups and $NH_2$ groups in the Q, $R^{6a}$, and $R^{6b}$ groups may be in the form of a salt (for example, hydrochloride).

In addition, a block copolymer including a hydrophilic polymer (polyethylene glycol) having a target binding site at the end can be synthesized by: synthesizing a block copolymer as mentioned above using a polyethylene glycol having a target binding site at the α-end; or synthesizing a block copolymer as mentioned above using a polyethylene glycol having a functional group capable of subsequently introducing a group including a target binding site into the α-end and then introducing the group including the target binding site. A variety of methods may be used as introduction methods for the group (s) including the target binding site (s); for example, by mixing in an acidic solution a block copolymer, which has a polyethylene glycol chain acetalized at the α-end, and a compound, which has a desired target binding site and a cysteine terminus, the target binding site can be provided at the terminus of the polyethylene glycol chain side.

[B. Complex]

Complexes of the present invention are complexes of the block copolymers described in the above section A and a biopolymer. The complexes may be a PIC of a plurality of the block copolymers and the biopolymers. In addition, the PIC may have the form of a polymer micelle in which the biopolymers are encapsulated in the plurality of the block copolymers. Although conventional carriers have the problem in that the complex dissociates in a medium having an ion concentration almost the same as that of physiological conditions, complexes of the present invention excel in stability, and hence can maintain the form of the complex in the medium, and even in a medium containing a protein.

[B-1. Biopolymer]

Examples of the biopolymer include proteins, lipids, and nucleic acids. Herein, the proteins include peptides. Among the biopolymers, the block copolymer can suitably form a complex with a nucleic acid. In addition, as biopolymers suitable for the formation of a complex, anionically-charged compounds, which have a negative charge at a pH equal to or lower than the pKa of the block copolymer, can be given as examples.

As mentioned above, by providing the block copolymer(s) with (a) cationic group(s) in (a) side chain(s) of the amino acid(s) in the polyamino acid chain segment, the block copolymer(s) can form a stable complex (for example, vesicle or aggregate) under physiological conditions, even with low molecular weight nucleic acids. As nucleic acids capable of forming a complex with the block copolymer, poly- or oligonucleotides including nucleotides formed of purine or pyrimidine bases, pentose, and phosphoric acid as basic units are meant; oligo- or poly-double-stranded RNA, oligo- or poly-double-stranded DNA, oligo- or poly-single-stranded DNA, and oligo- or poly-single-stranded RNA can be mentioned as examples. Further, oligo- or poly-double-stranded nucleic acids and oligo- or poly-single-stranded nucleic acids, in each of which RNA and DNA exist in a mixed state in the same chain, are also included. The nucleotides contained in the nucleic acids may be of a natural type or of a chemically modified non-natural type, or may have added thereto an amino group, a thiol group, a fluorescent compound, or any other molecule.

In case the nucleic acid is RNA, the RNA includes a 3'-terminus ribose having a 1,2-cis-diol, and hence can be bound to the block copolymer reversibly covalently via the substituted PBA group(s) as well as by electrostatic interactions with the cationic group(s) of the cationic amino acid residue. As a result, a complex that excels in stability is obtained. In such complexes that excel in stability, replacement of RNA molecules with glucose (having a cis-diol structure in its molecule) at blood concentration levels (usually, about 4 to 7 mM) can be avoided, and hence they excel in stability in blood. Therefore, in case the complex is administered in vivo, the retention properties in blood may be improved. In particular, in case the nucleic acid is double-stranded RNA, a cross-linked structure having as a binding site 3'-terminal ribose of each chain may be formed in the micelle, and hence a complex that excels exceedingly in stability can be obtained. In addition, incase the complex with the RNA is taken up into an endosome, which is a low-pH environment, hydrophobic interactions increase by hydrophobizing the substituted PBA groups, resulting in further improved stability. Further, after transfer from the endosome to the cytoplasm, the RNA can be released rapidly by substituting another molecule that is present in the cytoplasm at a relatively high concentration and has a 1,2-cis-diol, such as ATP or ribonucleic acid.

The strand length of the nucleic acid may be, for example, 4 to 20,000 bases, preferably 10 to 10,000 bases, more preferably 18 to 30 bases.

In consideration of the actions or functions thereof, plasmid DNA, siRNA, micro RNA, shRNA, antisense nucleic acids, decoy nucleic acids, aptamers, and ribozymes can be given as examples of the nucleic acid.

The ratio of the content of the block copolymer to the content of the biopolymer in the complex of the present invention may be appropriately set depending on the types of the block copolymer and the biopolymer, the application of the complex, or the like. In case the biopolymer is siRNA, the complex of the present invention has an N/P ratio of preferably 2 or more from the viewpoint of improving stability under physiological conditions, and has an N/P ratio of preferably 200 or less from the viewpoint of suppressing toxicity due to the polymer. It should be noted that the N/P ratio means [concentration of amino group(s) of the polyamino acid side chain in the block copolymer contained in the complex]/[concentration of phosphate group (s) in the nucleic acid]. Further, from the viewpoint of improving stability under physiological conditions, in case the biopolymer is siRNA, the complex of the present invention may have [number of positive charges in the polyamino acid chain segment]/[the total of the number of negative charges in the polyamino acid chain segment and the number of negative charges in the siRNA] at pH 7.4 of, for example, 1/2 to 20/1, preferably 1/1 to 10/1.

The block copolymer may maintain high hydrophilicity by appropriately selecting the types of substituted PBA groups and the number of the groups introduced, and hence the complex of the present invention can be prepared, for example, merely by mixing the block copolymer and the biopolymer in an aqueous solution, buffered as necessary. That is, the complex of the present invention may have the advantages in that it is not necessary to further modify the terminus of the block copolymer and in that the complex can be prepared by a simple method.

EXAMPLES

Hereinafter, although the present invention will be described concretely by way of Examples, the present invention is not limited to the Examples below. It should be noted that in the Examples below, polymer structures are described in the order of "the molecular weight (kDa) of PEG-the number of the FPBA group-containing amino acid residues/the total number of the amino acid residues constituting the polyamino acid chain segment". For example, in case PEG has a molecular weight of 10,000 and the polyamino acid chain segment is a polyamino acid chain segment obtained by introducing 5 FPBA groups into polylysine having a polymerization degree of 40, the polymer is referred to as "PEG-PLL 10-5/40". Further, for example, in case PEG has a molecular weight of 10,000 and the polyamino acid chain segment is polylysine that has no FPBA group introduced and has a polymerization degree of 40, the polymer is referred to as "PEG-PLL 10-0/40". In this context, each number in the notation is an average value over all of the block copolymers.

[Preparation of Polylysine-Based Block Copolymer]

Synthesis scheme A for a polylysine-based block copolymer used in the following experimental example is shown below. Specifically, the block copolymer was prepared as mentioned in (1-i) to (1-iii).

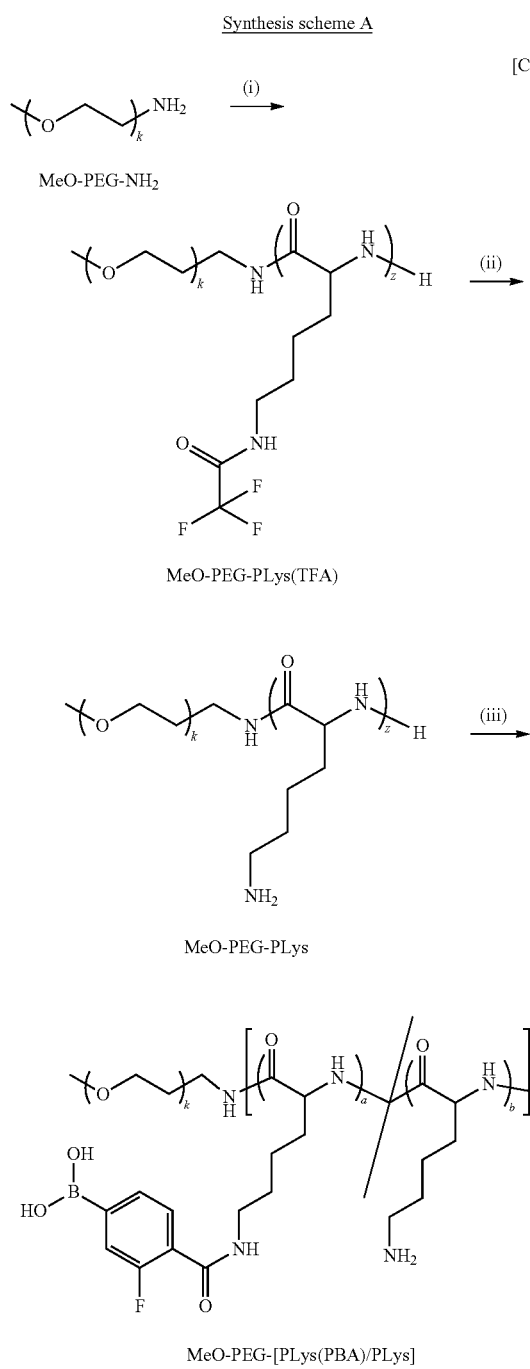

(1-i) Methoxy-PEG-NH$_2$ is lyophilized from benzene and dissolved in dimethylformamide (DMF) containing 1M thiourea. To the resultant solution is added NCA-Lys (TFA) dissolved in DMF containing 1M thiourea; by stirring the mixture for 3 days at 25° C., it undergoes polymerization. After the polymerization, the reaction solution is added dropwise to diethyl ether, and the resultant precipitates are collected by filtration and dried under reduced pressure to afford MeO-PEG-PLys (TFA).

(1-ii) MeO-PEG-PLys (TFA) is stirred in 1N NaOHaq./methanol=1/10 at 35° C. for 12 hours; the solution is subjected to dialysis (external solution: water) and lyophilized to afford MeO-PEG-PLys.

(1-iii) MeO-PEG-PLys and D-Mannitol, in an amount of 5 equivalents relative to the amino groups of PLys, are dissolved in a 50 mM NaHCO$_3$ aqueous solution. To the resultant solution is added 3-fluoro-4-carboxyphenylboronic acid dissolved in methanol, and a condensing agent DMT-MM is added thereto. The resultant solution is stirred at room temperature overnight, subjected to dialysis (external solution: water), and lyophilized to afford MeO-PEG-[PLys (FPBA)/PLys].

The molecular weight of the resultant block copolymer was measured by gel permeation chromatography (GPC). At that time, a solution obtained by dissolving D-sorbitol in 50 mM NaHCO$_3$ at 50 mg/mL or more, a phosphate buffer (pH 5 to 7), or a mixed solvent of a 500 mM NaCl aqueous solution containing 50 mg/mL D-sorbitol and methanol (NaCl aq./methanol=1/4) was used as the mobile phase. Further, the amount of FPBA group (s) introduced was estimated from an integration ratio of the side chain(s) to the phenyl ring(s) by $^1$H-NMR spectra. At that time, a solution obtained by dissolving the polymer in D$_2$O containing a small amount of D-sorbitol was used as the measurement sample.

[Preparation of PAsp(DET)-Based Block Copolymer]

Synthesis scheme B for a PAsp(DET)-based block copolymer used in the following experimental example is shown below. Specifically, the block copolymer was prepared as mentioned in (2-i) to (2-iii).

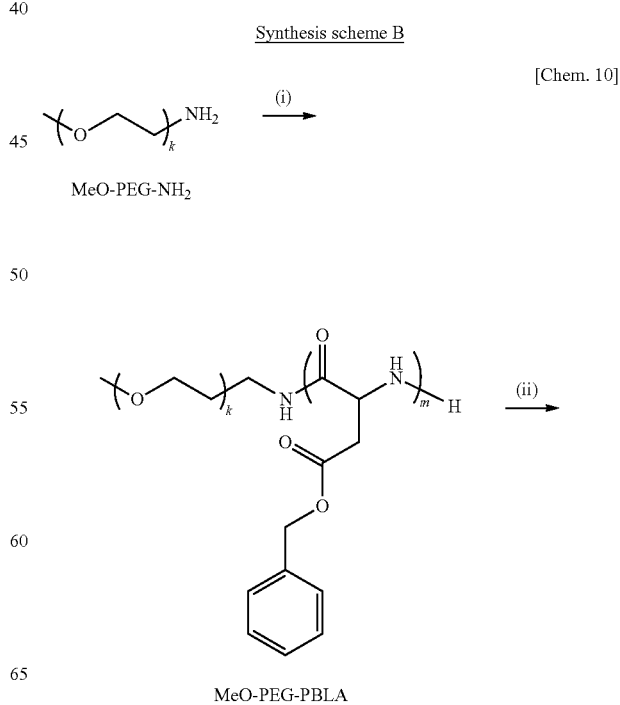

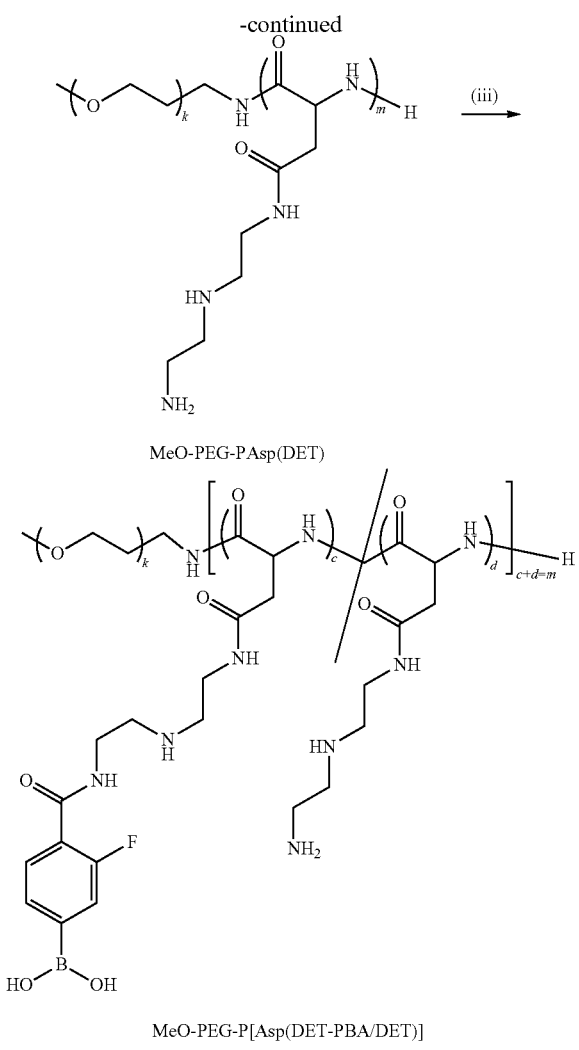

MeO-PEG-PAsp(DET)

MeO-PEG-P[Asp(DET-PBA/DET)]

(2-i) Methoxy-PEG-NH$_2$ is lyophilized from benzene and dissolved in dichloromethane. NCA-BLA dissolved in DMF/dichloromethane=1/10 is added to the resultant solution; by stirring the mixture for 3 days at 35° C., it undergoes polymerization. After the polymerization, the reaction solution is added dropwise to diethyl ether, and the resultant precipitates are collected by filtration and dried under reduced pressure to afford MeO-PEG-PBLA.

(2-ii) MeO-PEG-PBLA is lyophilized from benzene and dissolved in N-methyl-2-pyrrolidone (NMP). The resultant solution is added dropwise to a solution of diethylenetriamine in NMP, and the mixture is stirred at 5 to 10° C. for 1 hour. The resultant mixture is neutralized with hydrochloric acid under ice cooling, subjected to dialysis (external solution: 0.01N hydrochloric acid), and lyophilized to afford MeO-PEG-PAsp(DET).

(2-iii) MeO-PEG-PAsp(DET) and D-Mannitol, in an amount of 5 equivalents relative to the primary amines of PAsp(DET), are dissolved in a 50 mM NaHCO$_3$ aqueous solution under ice cooling (0° C.). To the resultant solution is added 3-fluoro-4-carboxyphenylboronic acid dissolved in methanol, and a condensing agent DMT-MM is added thereto. The resultant solution is stirred for 6 hours, subjected to dialysis at 5° C. (external solution: 0.01N hydrochloric acid, optionally containing sorbitol), and lyophilized to afford MeO-PEG-P[Asp (DET-FPBA/DET)].

The molecular weight of the resultant block copolymer was measured by gel permeation chromatography (GPC). At this time, a solution obtained by dissolving D-sorbitol in a 50 mM phosphate buffer (pH 7.4) at 50 mg/mL was used as the mobile phase. Further, the amount of FPBA group (s) introduced was estimated from an integration ratio of the side chain (s) to the phenyl ring (s) by $^1$H-NMR spectra. At this time, a solution obtained by dissolving the polymer in D$_2$O and containing a small amount of NaOD was used as the measurement sample.

[siRNA]

Sequences of siRNAs used in the following experimental examples are as follows. Labels such as Cy3 were introduced at the 5' ends of all of the sense strands.

(1) hVEGF-siRNA (siRNA for Human Vascular Endothelial Growth Factor):

(SEQ ID NO: 1)
Sense strand: 5'-GAUCUCAUCAGGGUACUCCdTdT-3'

(SEQ ID NO: 2)
Antisense strand: 5'-GGAGUACCCUGAUGAGAUCdTdT-3'

(2) Scramble-siRNA (siRNA Having a Sequence for Non-therapeutic Use):

(SEQ ID NO: 3)
Sense strand: 5'-UUCUCCGAACGUGUCACGUUU-3'

(SEQ ID NO: 4)
Antisense strand: 5'-ACGUGACACGUUCGGAGAAUU-3'

(3) GL3-siRNA (siRNA for Firefly Luciferase)

(SEQ ID NO: 5)
Sense strand: 5'-CUUACGCUGACUACUUCGAUU-3'

(SEQ ID NO: 6)
Antisense strand: 5'-UCGAAGUACUCAGCGUAAGUU-3'

[Relationship Between FPBA Group Content and Complex Stability]

A variety of block copolymers having different amino acid polymerization degrees and FPBA group contents were prepared as mentioned in Sections (1-i) to (1-iii) and (2-i) to (2-iii). It should be noted that PEG having a molecular weight (Mw) of 12,000 was used as methoxy-PEG-NH$_2$. The block copolymers were mixed with siRNA fluorescently labeled with Cy3 so as to achieve an N/P ratio of 8. The resultant mixtures were left to stand still in a refrigerator for 1 to 2 hours and diluted with a serum solution (150 mM NaCl, 10 mM Hepes, 10% FBS) so as to achieve an siRNA concentration of 50 nM. The resultant diluted solutions were left to stand still at room temperature for about 1 hour, and the siRNA diffusion time was measured with a confocal laser scanning microscope (manufactured by Carl Zeiss, product name "LSM510") (10 sec×10 times). Table 1 and FIG. 1 show the results. It should be noted that, when the measurement was carried out in the same manner as above except that siRNA was not mixed with the block copolymer, the diffusion time (diffusion time of siRNA alone) was 157.5 μsec. It should be noted that GL3-siRNA was used as the siRNA.

TABLE 1

PLys-based block copolymer

| | | | | | | | | | | |
|---|---|---|---|---|---|---|---|---|---|---|
| Molecular weight of PEG chain | 12,000 | | | | | | | | | |
| Total number of amino acid residues in polyamino acid chain segment | 21 | | 43 | | | | | 54 | | |
| Number of cationic amino acid residues free of FPBA group in polyamino acid chain segment | 18.0 | 16.3 | 43.0 | 35.3 | 32.9 | 28.8 | 24.1 | 51.1 | 43.3 | 38.1 |
| Number of FPBA groups in polyamino acid chain segment | 3.0 | 4.7 | 0.0 | 7.7 | 10.1 | 14.2 | 18.9 | 2.9 | 10.7 | 15.9 |
| Diffusion time [μsec, N/P = 8] | 323.3 | 331.4 | 298.6 | 321.1 | 440.2 | 773.4 | 783.6 | 337.0 | 434.9 | 1002.2 |
| √(Number of cationic amino acid residues free of FPBA group) + 2√(Number of FPBA groups) | 7.7 | 8.4 | 6.6 | 11.5 | 12.1 | 12.9 | 13.6 | 10.6 | 13.1 | 14.1 |
| Molecular weight of PEG chain | 12,000 | | | | | | | | | |
| Total number of amino acid residues in polyamino acid chain segment | 74 | | | | | | 106 | | | |
| Number of cationic amino acid residues free of FPBA group in polyamino acid chain segment | 74.0 | 70.7 | 68.2 | 65.9 | 62.1 | 56.9 | 106.0 | 104.5 | 101.9 | 93.7 |
| Number of FPBA groups in polyamino acid chain segment | 0.0 | 3.3 | 5.8 | 8.1 | 11.9 | 17.1 | 0.0 | 1.5 | 4.1 | 12.3 |
| Diffusion time [μsec, N/P = 8] | 379.1 | 1326.2 | 553.1 | 764.2 | 1073.0 | 1238.9 | 382.4 | 2120.6 | 1778.7 | 2896.3 |
| √(Number of cationic amino acid residues free of FPBA group) + 2√(Number of FPBA groups) | 8.6 | 12.1 | 13.1 | 13.8 | 14.8 | 15.8 | 10.3 | 12.7 | 14.2 | 16.7 |

PAsp (DET) -based block copolymer

| | | | | | | |
|---|---|---|---|---|---|---|
| Molecular weight of PEG chain | 12,000 | | | | | |
| Total number of amino acid residues in polyamino acid chain segment | 35.6 | 33.9 | 34.5 | 57.4 | 74.1 | 74.0 |
| Number of cationic amino acid residues free of FPBA group in polyamino acid chain segment | 32.9 | 23.7 | 14.5 | 48.1 | 69.9 | 67.0 |
| Number of FPBA groups in polyamino acid chain segment | 2.6 | 10.2 | 20.0 | 9.3 | 4.2 | 7.0 |
| Diffusion time [μsec, N/P = 8] | 313.3 | 367.6 | 807.8 | 1241.9 | 1622.6 | 1417.7 |
| √(Number of cationic amino acid residues free of FPBA group) + 2√(Number of FPBA groups) | 9.0 | 11.3 | 12.7 | 13.0 | 12.4 | 13.5 |

As shown in Table 1 and FIG. 1, when siRNA is mixed with the block copolymers, the siRNA diffusion time was longer than that when siRNA was used alone. Therefore, all of the block copolymers were found to form complexes with siRNA. In addition, the diffusion time with the block copolymers having the FPBA group(s) introduced was longer than that with the block copolymers that were free of the FPBA group, and hence the block copolymers having the FPBA group(s) introduced were found to form more stable complexes. Of those, when the block copolymers satisfying the relationship of [√(the number of cationic amino acid residues free of the FPBA group in the polyamino acid chain segment)+2√(the number of FPBA groups in the polyamino acid chain segment)≥12.0] were used, the siRNA diffusion time was 400 μsec or more, suggesting that highly stable complexes were formed.

[Block Copolymer Toxicity Test]

Figure 2:
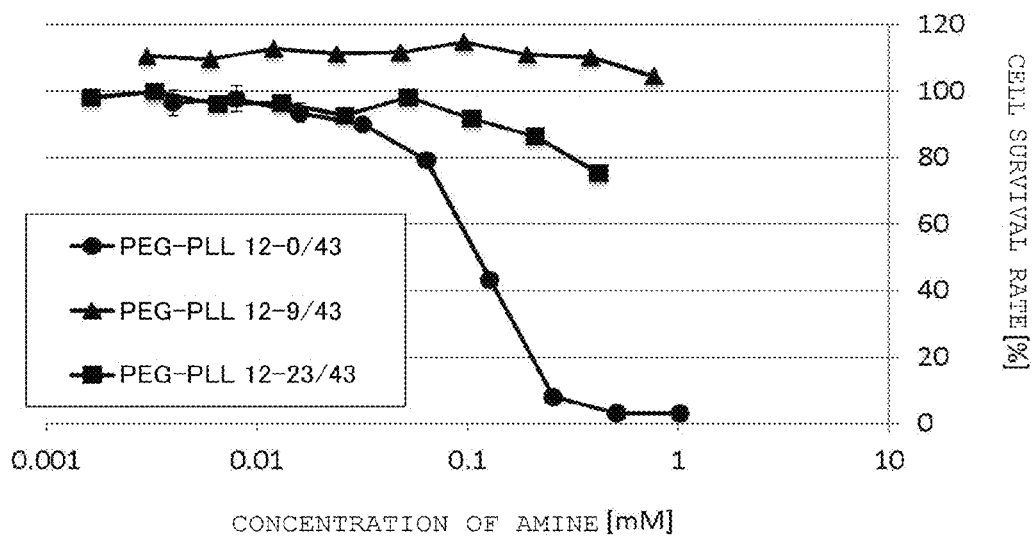
FIG. 2 is a graph showing the results of a toxicity test of block copolymers.

A549-Luc cells were seeded in a 96-well culture dish at 2,500 cells/well and cultured in a DMEM medium containing 10% fetal bovine serum in an incubator for 24 hours. The medium was exchanged for fresh DMEM medium containing 10% fetal bovine serum, and each of the block copolymers dissolved in physiological saline was added at different amine concentrations. Subsequently, the cells were cultured for 48 hours, the number of living cells were measured with a "Cell Counting Kit 8" (product name, manufactured by Dojindo Molecular Technologies, Inc.), and the cell survival rate thereof was calculated (N=4). FIG. 2 shows the results.

[Complex Toxicity]

Figure 3:
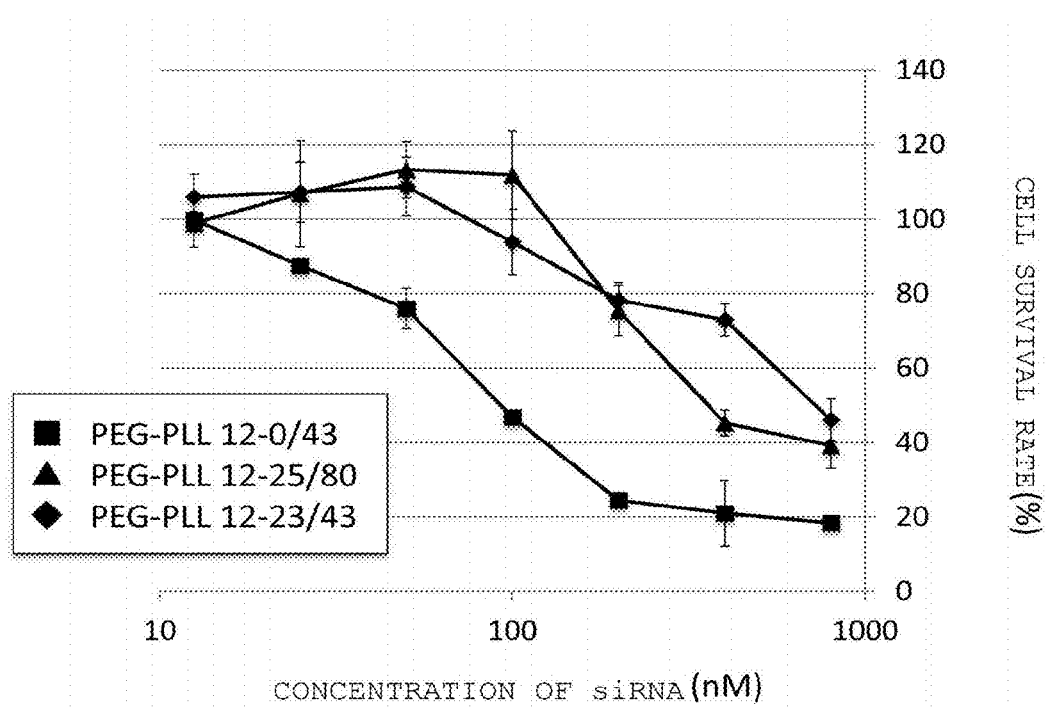
FIG. 3 is a graph showing the results of a toxicity test of complexes.

A549-Luc cells were seeded in a 96-well culture dish at 2,500 cells/well and cultured in a DMEM medium containing 10% fetal bovine serum in an incubator for 24 hours. The medium was exchanged for fresh DMEM medium containing 10% fetal bovine serum, and each of the complexes of siRNA and the block copolymers was added at different siRNA concentrations. Subsequently, the cells were cultured for 48 hours, the number of living cells were measured with a "Cell Counting Kit 8" (product name, manufactured by Dojindo Molecular Technologies, Inc.), and the cell survival rate thereof was calculated (N=4). FIG. 3 shows the results. It should be noted that the complexes were prepared by: adding the block copolymers and GL3-siRNA to a 10 mM HEPES buffer (pH 7.3) so as to achieve an N/P ratio of 4 and an siRNA concentration of 80 nM; mixing the resultant; leaving the mixture to stand still for about 1 to 2 hours at room temperature; and diluting the mixture to different concentrations.

As shown in FIG. 2, the groups treated with the block copolymers having the FPBA groups introduced had higher cell survival rates as compared to the group treated with the block copolymer having no FPBA group introduced. In addition, as shown in FIG. 3, the groups treated with the complexes including the block copolymers having the FPBA groups introduced had higher cell survival rates as compared to the group treated with the complex including the block copolymer having no FPBA group introduced. The results reveal that the introduction of the FPBA groups causes no cytotoxicity, and the block copolymers having the FPBA groups introduced have satisfactory biocompatibility.

[Evaluation of pH Stability of Complex]

Figure 4:
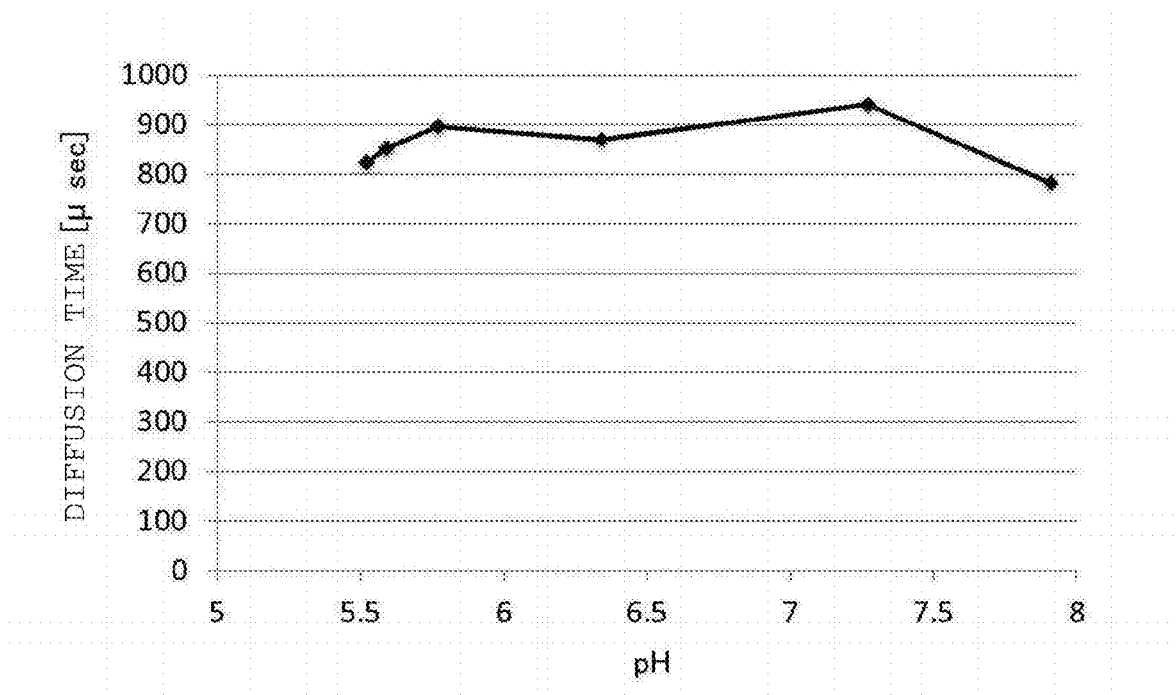
FIG. 4 is a graph showing pH stability of a complex.

A block copolymer (PEG-PLL 12-23/43) and GL3-siRNA labeled with Cy3 were dissolved in buffers (phosphate buffer or phosphate-citrate buffer) having a variety of pH values, and mixed so as to achieve an N/P ratio of 4 and an siRNA concentration of 50 nM. The resultant mixtures were left to stand still for about 1 hour at room temperature, and the siRNA diffusion time was measured with a confocal laser scanning microscope (manufactured by Carl Zeiss, product name "LSM510") (10 sec×10 times). FIG. 4 shows the results.

As shown in FIG. 4, the siRNA diffusion time was longer than 800 μsec over a wide pH range of from an in vivo environment (about pH 7.4) to an acidic environment (about pH 5.5) of the inside of an endosome or the like. Therefore, the block copolymers of the present invention were found to be able to form stable complexes with siRNA (siRNA-encapsulated polymer micelle) over the above-mentioned pH range.

[Evaluation of siRNA-Releasing Properties of Complex]

Figure 5:
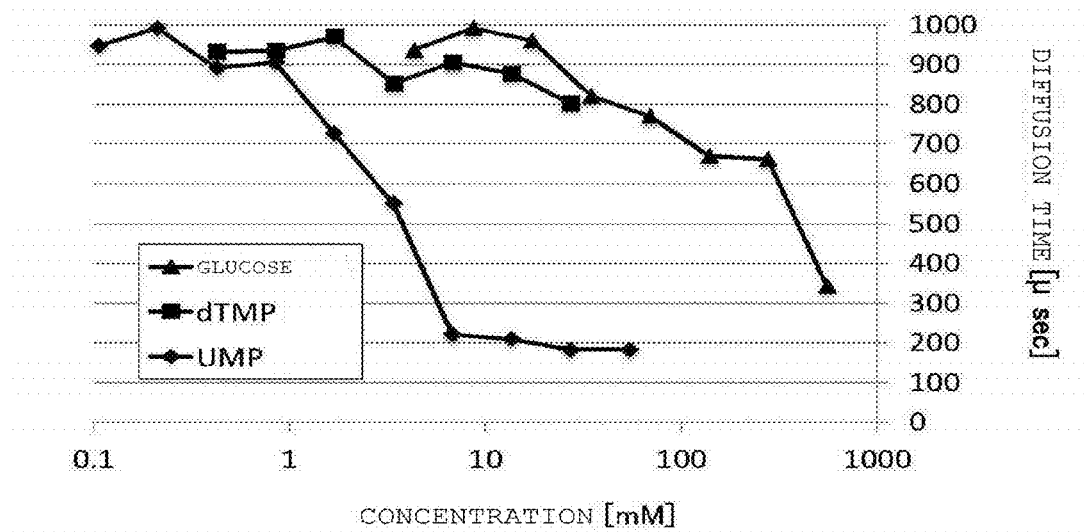
FIG. 5 is a graph showing siRNA-releasing properties of complexes.

The block copolymer (PEG-PLL 12-23/43) and GL3-siRNA labeled with Cy3 were separately dissolved in a 10 mM HEPES buffer (pH 7.3), and mixed so as to achieve an N/P ratio of 4. The resultant mixtures were left to stand still for about 1 to 2 hours in a refrigerator, and diluted with 10 mM HEPES buffers (pH 7.3) containing a variety of concentrations of glucose, dTMP, or UMP so as to achieve an siRNA concentration of 50 nM. The resultant diluted solutions were left to stand still at room temperature for about 1 hour. Subsequently, the siRNA diffusion time was measured with a confocal laser scanning microscope (manufactured by Carl Zeiss, product name "LSM510") (10 sec×10 times). FIG. 5 shows the results.

As shown in FIG. 5, the siRNA diffusion time at glucose concentrations almost the same as those in blood (usually, about 4 to 7 mM) is longer than 800 μsec, which shows that the block copolymers of the present invention can form stable complexes with siRNA (siRNA-encapsulated polymer micelle) in blood. In addition, when the glucose concentrations are higher than that in blood, the diffusion time gradually becomes shorter, suggesting that the micelles collapse at such concentrations to rapidly release siRNA. It should be noted that it is surmised that such a collapse of the micelles occurs by substitution of RNA molecules, which are bound to the FPBA groups via the 1,2-diol structures in the micelles, with glucoses having a 1,2-diol structure similar to the RNA molecules.

Similarly, it was found that the micelle shape can be maintained in the presence of UMP having the 1,2-diol structure at low UMP concentrations, but the micelles collapse at UMP concentrations higher than 1 mM by substitution of the RNA molecules with UMP to rapidly release siRNA. On the other hand, the micelle shape can be maintained stably in the presence of dTMP having a structure similar to UMP but having no 1,2-diol structure, even at dTMP concentrations higher than 10 mM. This is probably because no substitution of the RNA molecules occurs.

[Evaluation of Intracellular Uptake Ability of Complex]

Figure 6:
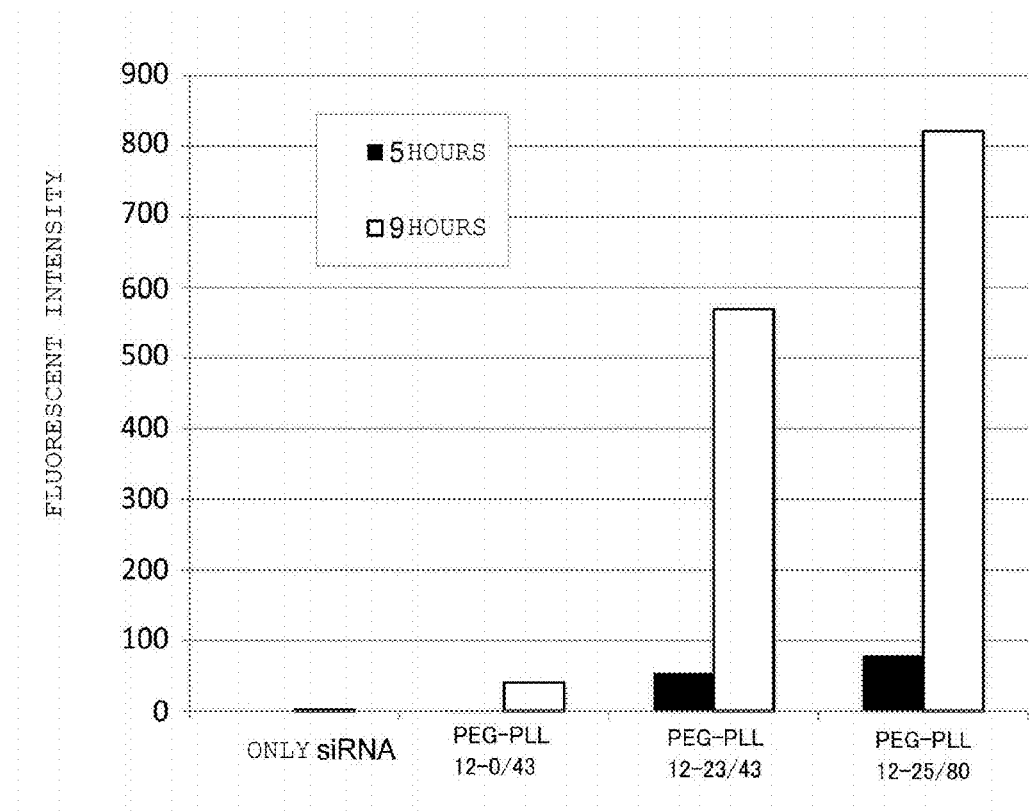
FIG. 6 is a graph showing the uptake of complexes into cells.

A549-Luc cells were seeded in a 48-well dish at 10,000 cells/well, and cultured for 24 hours in an incubator with a DMEM medium containing 10% fetal bovine serum. The medium was exchanged for fresh DMEM medium containing 10% fetal bovine serum, and siRNA labeled with Cy3 or a complex of the siRNA and a block copolymer was added to the medium so that the concentration of siRNA was 100 nM/well. After having been cultured in an incubator at 37° C. for 5 hours or 9 hours, the cells were washed three times with 1 mL of a PBS buffer, and detached from the dish with a trypsin-EDTA solution. The detached cells were subjected to histogram analysis using a flow cytometer (manufactured by BD, LSRII) in which a Cy3 filter was set. Thus, the amount of siRNA taken up into the cells was evaluated (N=4). It should be noted that GL3-siRNA was used as the siRNA. FIG. 6 shows a graph that shows the amount of siRNA taken up into the cells. It should be noted that the complex was prepared by adding each block copolymer and siRNA to a 10 mM HEPES buffer (pH 7.3) so as to achieve an N/P ratio of 8 and an siRNA concentration of 4 μM, mixing the resultant, and leaving the mixture to stand still for about 1 to 2 hours at room temperature.

As shown in FIG. 6, the amounts of siRNA taken up in case siRNA was added as a complex with the block copolymer having the FPBA group introduced were dramatically improved as compared to those in case siRNA was added alone and in case siRNA was added as a complex with the block copolymer having no FPBA group introduced.

[Evaluation of Blood Retention Properties of Complex]

Figure 7:
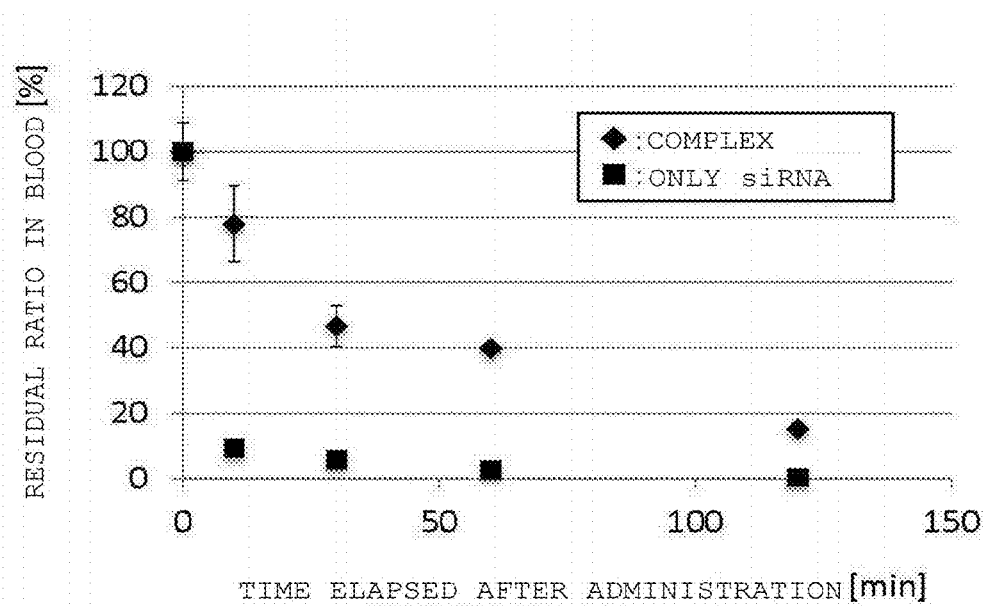
FIG. 7 is a graph showing retention properties of a complex in blood.

The block copolymer (PEG-PLL 12-23/43) and Cy5-GL3-siRNA were added to a 10 mM HEPES buffer (pH 7.3) so as to achieve an N/P ratio of 8 and an siRNA concentration of 7.5 μM, and the resultant was mixed and left to stand still for about 1 to 2 hours at room temperature to prepare a complex solution. The complex solution or a solution of the siRNA (10 mM HEPES buffer) was administered to the tail veins of mice (female Balb/C nude, 6-week-old, N=4) so that the dose was 20 μg of the siRNA, and the amount of the siRNA remaining in blood was determined over time. FIG. 7 shows the results.

As shown in FIG. 7, in case the siRNA was administered alone, only about 10% of the siRNA remained at 10 minutes after administration, and almost no siRNA remained after a lapse of 1 hour. On the other hand, in case the siRNA was administered as the complex, 40% or more of the siRNA remained at 1 hour after administration, and 10% or more of the siRNA remained even after a lapse of 2 hours. This suggests that the complex including the block copolymer of the present invention and siRNA (siRNA-encapsulated micelle) excels exceedingly in retention properties in blood.

[Evaluation of Anticancer Activity of Complex]

(1) Preparation of FPBA Group-Containing Block Copolymer

A block copolymer Ace-PEG-PAsp(DET) 12-62/75 was obtained by a scheme similar to Scheme B. Specifically, Ace-PEG-PBLA (12-110) having an acetal group at the terminus on the PEG side was subjected to aminolysis with DET to afford Ace-PEG-PAsp(DET) (12-90). Subsequently, dialysis was carried out against an NaCl solution to convert acidic acid serving as a counterion into chloride, and 4-carboxy-3-fluorophenylboronic acid was condensed using a condensing agent (DMT-MM) to afford the block copolymer Ace-PEG-PAsp(DET) 12-62/75.

(2) Preparation of cRGD-Introduced Block Copolymer

Subsequently, cRGD peptide (Cyclic (Arg-Gly-Asp-D-Phe-Cys)) was mixed with DTT in an amount of 5 equivalents relative to the acetal group at pH 7.2 for 1 hour, the resultant mixture and the block copolymer were mixed, and the pH was adjusted to 2. The mixture was stirred for 1 hour, and the pH was adjusted to 5 with 2 M sodium acetate and NaOH. After that, water was added thereto so as to achieve a polymer concentration of 20 mg/mL, and the mixture was stirred overnight. Dialysis was carried out against pure water to remove unreacted products and unwanted substances, followed by lyophilization to afford a block copolymer cRGD-PEG-PAsp (DET) 12-62/75 having cRGD introduced at the terminus of the PEG chain. It should be noted that the reaction and the dialysis were carried out at 4° C. (refrigerator).

(3) Preparation of Complex

Block copolymers were dissolved in a 10 mM HEPES buffer so as to achieve a concentration of 10 mg/mL. 12.18 μL of the polymer solutions, 75 μL of siRNA (15 μM in a 10 mM HEPES buffer), and 7.81 μL of a 10 mM HEPES buffer were mixed, and the mixtures were left to stand still overnight. Several hours prior to administration, 5 μL of 3 M NaCl in a 10 mM HEPES buffer were added to the mixtures, and the concentration of NaCl was adjusted to 150 mM (total volume:

100 μL). Thus, complexes (siRNA-encapsulated polymer micelles) were obtained. Table 2 shows combinations of siRNA and the block copolymers and mixing ratios in the complexes prepared.

TABLE 2

| Complex | Block copolymer | siRNA | Mixing ratio[*1] | Average diameter |
|---|---|---|---|---|
| (+)hVEGF | cRGD-PEG-PAsp (DET) 12-62/75 | siRNA-hVEGF | 5 | — |
| (−)hVEGF | Ace-PEG-PAsp (DET) 12-62/75 | siRNA-hVEGF | 5 | 39.95 nm |
| (+)Scramble | cRGD-PEG-PAsp (DET) 12-62/75 | siRNA-Scramble | 5 | — |

[*1]Ratio of the number of positive charges of the polyamino acid chain segment to the total of number of negative charges of the polyamino acid chain segment and the number of negative charges of the siRNA (positive charges/total of negative charges) at pH 7.4

Figure 8:
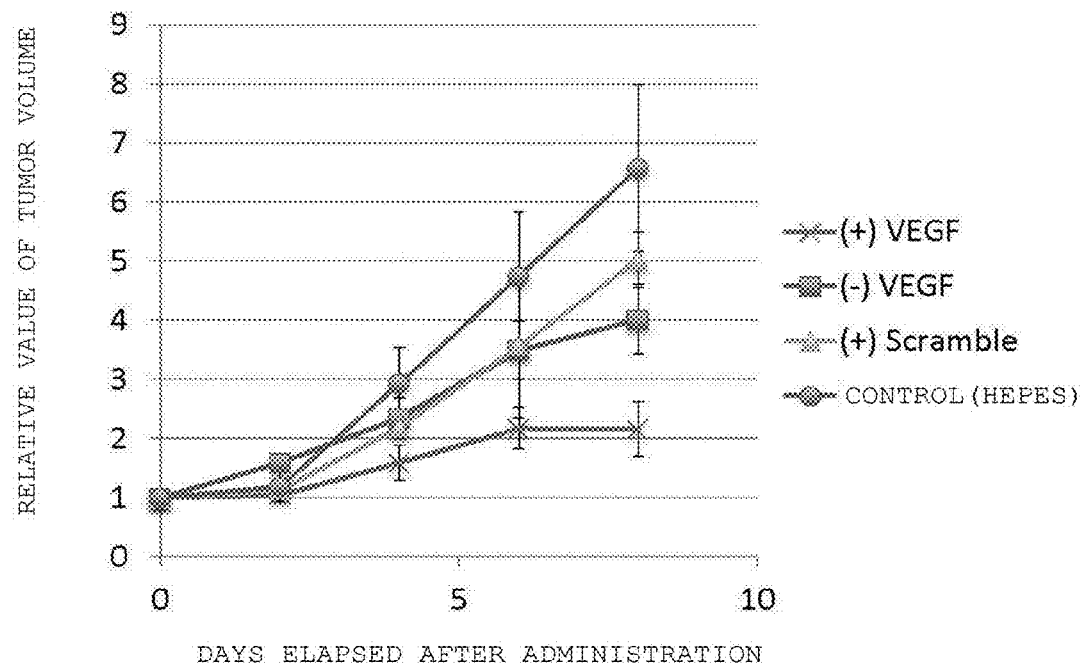
FIG. 8 is a graph showing anticancer activities of complexes.

(4) Evaluation of Anticancer Activity 6-week-old mice (female Balb/C nude, N=4) were purchased and fed for 1 week, and HeLa-luc cells adjusted to $5.0 \times 10^7$ cells/mL were injected subcutaneously in an amount of 100 μL per mouse. After that, the mice were further fed for 4 days, and treatment (i.e., administration of the complexes) was started. Specifically, the complex prepared in (3) above was administered to the tail veins of the mice every other day until day 6 (i.e., when the administration start date was defined as day 0, the complex was administered four times in total on day 0, day 2, day 4, and day 6). The siRNA was administered at a dose of 15 μg/100 μL. To a control group, a HEPES solution was administered at a dose of 100 μL. FIG. 8 shows the relationship between a relative value of the tumor volume to the tumor volume on the administration start date, and the number of days elapsed after the administration.

As shown in FIG. 8, in the group to which the (−)hVEGF complex using as a carrier the block copolymer of the present invention in which the PEG terminus had no cRGD introduced was administered, growth of the tumor was clearly suppressed as compared to the control group and the group to which the (+)Scramble complex was administered. This reveals that siRNA was maintained stably in blood by the block copolymer and exhibited RNA interference ability. Further, the group to which the (+)hVEGF complex using as a carrier the block copolymer in which the PEG terminus had cRGD introduced was administered, growth of the tumor was significantly suppressed as compared to the control group and the group to which the (+)Scramble complex was administered. This reveals that the complex has a stability in blood that excels; furthermore, it is taken up into tumor tissues with a high transfer rate to efficiently exhibit the RNA interference effect.

INDUSTRIAL APPLICABILITY

The block copolymers of the present invention can be suitably applied in the DDS field.

The invention claimed is:

1. A pharmaceutical composition, comprising a complex of:
   a block copolymer having a polyamino acid chain segment and a hydrophilic polymer chain segment, and
   a nucleic acid,
   wherein the polyamino acid chain segment includes at least one amino acid residue having a side chain that contains a cationic group and at least one amino acid residue having a side chain that contains a substituted phenylboronic acid group,
   at least one hydrogen atom of the phenyl ring of the substituted phenylboronic acid group has been substituted so that the substituted phenylboronic acid group has a pKa of less than 8, and
   the nucleic acid is reversibly covalently bound to the substituted phenylboronic acid group.

2. The pharmaceutical composition according to claim 1, wherein the substituted phenylboronic acid group of the at least one amino acid residue has a pKa of less than 7.5.

3. The pharmaceutical composition according to claim 1, wherein the substituted phenylboronic acid group of the at least one amino acid residue comprises a fluorinated phenylboronic acid group having the following formula (I):

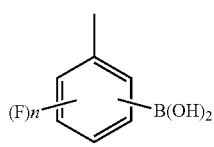

(I)

wherein the (each) F is present independently;
n is 1, 2, 3, or 4; and
with the proviso that when n is 1, F and B(OH)$_2$ may be bound to the phenyl ring in an ortho, meta, or para relationship.

4. The pharmaceutical composition according to claim 1, wherein the cationic group of the at least one amino acid residue is an amino group.

5. The pharmaceutical composition according to claim 1, wherein the cationic group of the at least one amino acid residue is a lysine residue or an amino acid residue, in which an —OH moiety of a carboxyl group (—C(=O)OH) of an acidic amino acid has been substituted with a group selected from any one the following formulas (i) to (iv):

$$-\text{NH}-(\text{CH}_2)_{p1}-[\text{NH}-(\text{CH}_2)_{q1}-]_{r1}\text{NH}_2 \quad \text{(i)};$$

$$-\text{NH}-(\text{CH}_2)_{p2}-\text{N}[-(\text{CH}_2)_{q2}-\text{NH}_2]_2 \quad \text{(ii)};$$

$$-\text{NH}-(\text{CH}_2)_{p3}-\text{N}\{[-(\text{CH}_2)_{q3}-\text{NH}_2][-(\text{CH}_2)_{q4}-\text{NH}-]_{r2}\text{H}\} \quad \text{(iii); and}$$

$$-\text{NH}-(\text{CH}_2)_{p4}-\text{N}\{-(\text{CH}_2)_{q5}-\text{N}[-(\text{CH}_2)_{q6}-\text{NH}_2]_2\}_2 \quad \text{(iv); and}$$

wherein p1 to p4, q1 to q6, and r1 and r2 are each independently an integer of 1 to 5.

6. The pharmaceutical composition according to claim 1, wherein the following relationship is satisfied:

$$\sqrt{A}+2\cdot\sqrt{B}\geq C,$$

wherein A is the number of cationic amino acid residue(s) in the polyamino acid chain segment that contain no substituted phenylboronic acid group,
B is the number of substituted phenylboronic acid group(s) in the polyamino acid chain segment and
C is 12.0.

7. The pharmaceutical composition according to claim 1, wherein the polyamino acid chain segment further includes at least one amino acid residue having a side chain containing a hydrophobic group.

8. The pharmaceutical composition according to claim 2, wherein the substituted phenylboronic acid group of the at least one amino acid residue comprises a fluorinated phenylboronic acid group having the following formula (I):

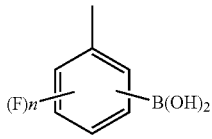
(I)

wherein the (each) F is present independently;

n is 1, 2, 3, or 4; and with the proviso that when n is 1, F and B(OH)$_2$ may be bound to the phenyl ring in an ortho, meta, or para relationship.

9. The pharmaceutical composition according to claim 8, wherein the cationic group of the at least one amino acid residue is an amino group.

10. The pharmaceutical composition according to claim 9, wherein the amino group is a lysine residue or an amino acid residue, in which an —OH moiety of a carboxyl group (—C(=O)OH) of an acidic amino acid has been substituted with a group selected from any one the following formulas (i) to (iv):

—NH—(CH$_2$)$_{p1}$—[NH—(CH$_2$)$_{q1}$—]$_{r1}$NH$_2$ (i);

—NH—(CH$_2$)$_{p2}$—N[—(CH$_2$)$_{q2}$—NH$_2$]$_2$ (ii);

—NH—(CH$_2$)$_{p3}$—N{[—(CH$_2$)$_{q3}$—NH$_2$][—(CH$_2$)$_{q4}$—NH-]$_{r2}$H} (iii); and —NH—(CH$_2$)$_{p4}$—N{—(CH$_2$)$_{q5}$—N[—(CH$_2$)$_{q6}$—NH$_2$]$_2$}$_2$ (iv); and wherein p1 to p4, q1 to q6, and r1 and r2 are each independently an integer of 1 to 5.

11. The pharmaceutical composition according to claim 10, wherein the following relationship is satisfied:

$\sqrt{A}+2\cdot\sqrt{B} \geq C$, wherein A is the number of cationic amino acid residue(s) in the polyamino acid chain segment that contain no substituted phenylboronic acid group, B is the number of substituted phenylboronic acid group(s) in the polyamino acid chain segment and C is 12.0.

12. The pharmaceutical composition according to claim 11, wherein the polyamino acid chain segment further includes at least one amino acid residue having a side chain containing a hydrophobic group.

13. The pharmaceutical composition according to claim 11, wherein the block copolymer is selected from the group consisting of the following formulas (1)-(4):

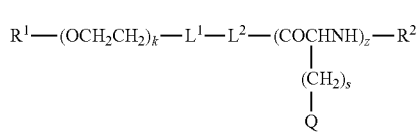
(1)

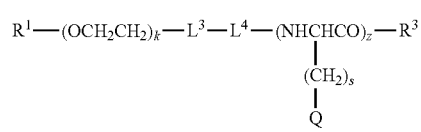
(2)

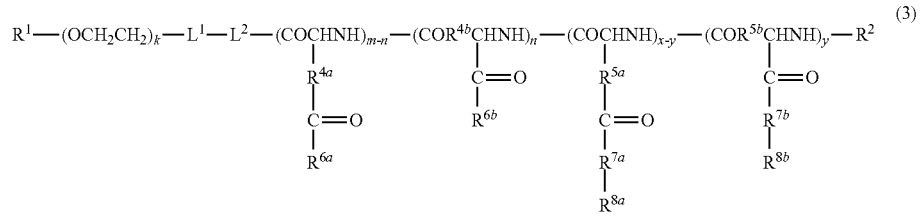
(3)

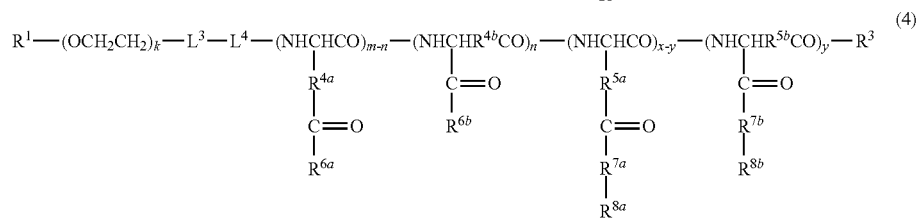
(4)

wherein:

R$^1$ is a hydrogen atom or an unsubstituted or substituted linear or branched alkyl group having 1 to 12 carbon atoms;

R$^2$ is a hydrogen atom, an unsubstituted or substituted linear or branched alkyl group having 1 to 12 carbon atoms, or an unsubstituted or substituted linear or branched alkylcarbonyl group having 1 to 24 carbon atoms;

R$^3$ is a hydroxyl group, an unsubstituted or substituted linear or branched alkyloxy group having 1 to 12 carbon atoms, an unsubstituted or substituted linear or branched alkenyloxy group having 2 to 12 carbon atoms, an unsubstituted or substituted linear or branched alkynyloxy group having 2 to 12 carbon atoms, or an unsubstituted or substituted linear or branched alkyl-substituted imino group having 1 to 12 carbon atoms;

$R^{4a}$, $R^{4b}$, $R^{5a}$, and $R^{5b}$ are each independently a methylene group or an ethylene group;

$R^{6a}$ and $R^{6b}$ are each independently a group selected from one of said formulas (i) to (iv);

$R^{7a}$ and $R^{7b}$ are each independently —O— or —NH—;

$R^{8a}$ and $R^{8b}$ are each independently a saturated or unsaturated linear or branched aliphatic hydrocarbon group having 6 to 27 carbon atoms, an aromatic hydrocarbon group having 6 to 27 carbon atoms, or a steryl group;

Q is —NH$_2$, —NHC(=NH)NH$_2$, or a group represented by the following formula (II):

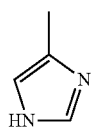

(II)

$L^1$ and $L^3$ are each independently —S—S— or a valence bond;

$L^2$ is —NH—, —O—, —O(CH$_2$)$_{p1}$—NH—, or -$L^{2a}$-(CH$_2$)$_{q1}$-$L^{2b}$-, where p1 and q1 are each independently an integer of 1 to 5, $L^{2a}$ is OCO, OCONH, NHCO, NHCOO, NHCONH, CONH, or COO, and $L^{2b}$ is NH or O;

$L^4$ is —OCO—(CH$_2$)$_{p2}$—CO—, —NHCO—(CH$_2$)$_{p3}$—CO—, or -$L^{4a}$-(CH$_2$)$_{q2}$—CO—, where p2, p3, and q2 are each independently an integer of 1 to 5, $L^{4a}$ is OCONH, —CH$_2$NHCO—, NHCOO, NHCONH, CONH, or COO;

k is an integer of 30 to 20,000;
s is an integer of 1 to 6;
m is an integer of 1 to 300;
n is an integer of 0 to m;
x is an integer of 0 to 80;
y is an integer of 0 to x;
z is an integer of 2 to 300;

the total number of primary amino groups and secondary amino groups included in all Q's is defined as w, the total number of primary amino groups and secondary amino groups included in (m-n) of group $R^{6a}$ and n of group $R^{6b}$ is also defined as w, and at least one, but less than w of, hydrogen atom(s) of said primary and secondary amino groups is (are) substituted with (an) acyl group(s) having the substituted phenylboronic acid group, with the proviso that the binding order of the amino acid residue(s) having the cationic side chain(s), the amino acid residue(s) containing the substituted phenylboronic acid group(s), and if present the amino acid residue(s) containing a hydrophobic side chain, is arbitrary.

14. The pharmaceutical composition according to claim 13, wherein k is 50-1500.

15. The pharmaceutical composition according to claim 14, wherein $R^1$ is a linear or branched alkyl group having 1 to 12 carbon atoms substituted with a target binding site.

16. The pharmaceutical composition according to claim 15, wherein the target binding site comprises a peptide having 1-100 amino acid residues.

17. The pharmaceutical composition according to claim 16, wherein z is 40-150.

18. The pharmaceutical composition according to claim 1, wherein the block copolymer is selected from the group consisting of the following formulas (1)-(4):

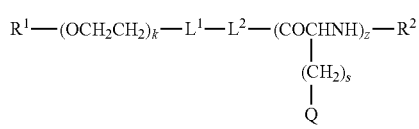

(1)

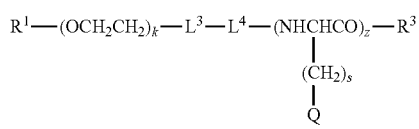

(2)

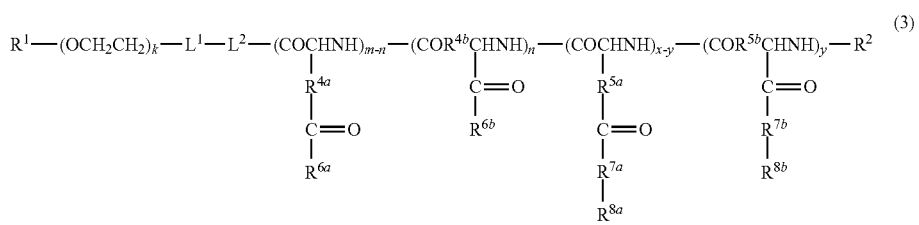

(3)

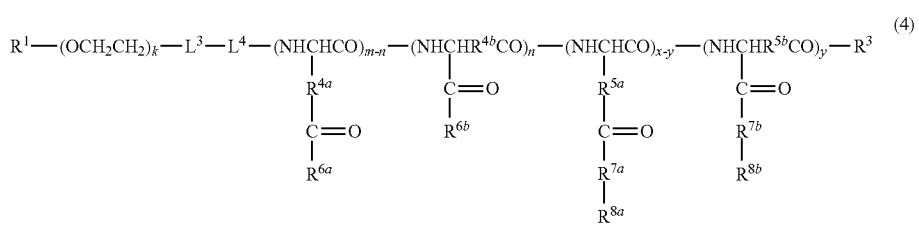

(4)

wherein:
- $R^1$ is a hydrogen atom or an unsubstituted or substituted linear or branched alkyl group having 1 to 12 carbon atoms;
- $R^2$ is a hydrogen atom, an unsubstituted or substituted linear or branched alkyl group having 1 to 12 carbon atoms, or an unsubstituted or substituted linear or branched alkylcarbonyl group having 1 to 24 carbon atoms;
- $R^3$ is a hydroxyl group, an unsubstituted or substituted linear or branched alkyloxy group having 1 to 12 carbon atoms, an unsubstituted or substituted linear or branched alkenyloxy group having 2 to 12 carbon atoms, an unsubstituted or substituted linear or branched alkynyloxy group having 2 to 12 carbon atoms, or an unsubstituted or substituted linear or branched alkyl-substituted imino group having 1 to 12 carbon atoms;
- $R^{4a}$, $R^{4b}$, $R^{5a}$, and $R^{5b}$ are each independently a methylene group or an ethylene group;
- $R^{6a}$ and $R^{6b}$ are each independently a group selected from following formulas (i) to (iv):

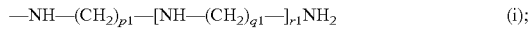  (i);

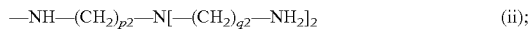  (ii);

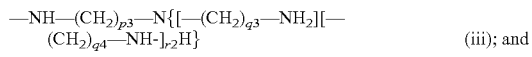  (iii); and

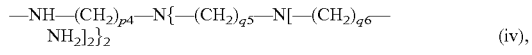  (iv), where p1 to p4, q1 to q6, and r1 and r2 are each independently an integer of 1 to 5,
- $R^{7a}$ and $R^{7b}$ are each independently —O— or —NH—;
- $R^{8a}$ and $R^{8b}$ are each independently a saturated or unsaturated linear or branched aliphatic hydrocarbon group having 6 to 27 carbon atoms, an aromatic hydrocarbon group having 6 to 27 carbon atoms, or a steryl group;
- Q is —NH$_2$, —NHC(=NH)NH$_2$, or a group represented by the following formula (II):

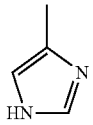 (II)

$L^1$ and $L^3$ are each independently —S—S— or a valence bond;
$L^2$ is —NH—, —O—, —O(CH$_2$)$_{p1}$—NH—, or -L$^{2a}$-(CH$_2$)$_{q1}$-L$^{2b}$-, where p1 and q1 are each independently an integer of 1 to 5, L$^{2a}$ is OCO, OCONH, NHCO, NHCOO, NHCONH, CONH, or COO, and L$^{2b}$ is NH or O;
$L^4$ is —OCO—(CH$_2$)$_{p2}$—CO—, —NHCO—(CH$_2$)$_{p3}$—CO—, or -L$^{4a}$-(CH$_2$)$_{q2}$—CO—, where p2, p3, and q2 are each independently an integer of 1 to 5, L$^{4a}$ is OCONH, —CH$_2$NHCO—, NHCOO, NHCONH, CONH, or COO;
- k is an integer of 30 to 20,000;
- s is an integer of 1 to 6;
- m is an integer of 1 to 300;
- n is an integer of 0 to m;
- x is an integer of 0 to 80;
- y is an integer of 0 to x;
- z is an integer of 2 to 300;
- the total number of primary amino groups and secondary amino groups included in all Q's is defined as w,
- the total number of primary amino groups and secondary amino groups included in (m-n) of group $R^{6a}$ and n of group $R^{6b}$ is also defined as w, and
- at least one, but less than w of, hydrogen atom(s) of said primary and secondary amino groups is (are) substituted with (an) acyl group(s) having the substituted phenylboronic acid group,
- with the proviso that the binding order of the amino acid residue(s) having the cationic side chain(s), the amino acid residue(s) containing the substituted phenylboronic acid group(s), and if present the amino acid residue(s) containing a hydrophobic side chain, is arbitrary.

19. A block copolymer comprising:
a polyamino acid chain segment and a hydrophilic polymer chain segment,
wherein the polyamino acid chain segment includes at least one amino acid residue having a side chain that contains a cationic group and at least one amino acid residue having a side chain that contains a substituted phenylboronic acid group,
at least one hydrogen atom of the phenyl ring of the substituted phenylboronic acid group has been substituted so that the substituted phenylboronic acid group has a pKa of less than 8, and
the following relationship is satisfied:

$$\sqrt{A}+2\cdot\sqrt{B}\geq 12.0$$

wherein A is the number of cationic amino acid residue(s) in the polyamino acid chain segment that contain no substituted phenylboronic acid group,
B is the number of substituted phenylboronic acid group(s) in the polyamino acid chain segment and
C is 12.0.

20. The block copolymer according to claim 19, wherein the block copolymer is selected from the group consisting of the following formulas (1)-(4):

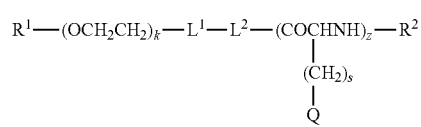 (1)

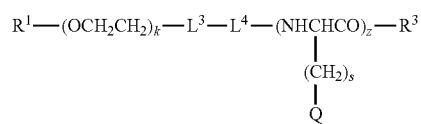 (2)

-continued $$R^1-(OCH_2CH_2)_k-L^1-L^2-(COCHNH)_{m-n}-(COR^{4b}CHNH)_n-(COCHNH)_{x-y}-(COR^{5b}CHNH)_y-R^2 \quad (3)$$

with side chains:
- on (COCHNH)$_{m-n}$: $R^{4a}$, then $C=O$, then $R^{6a}$
- on (COR$^{4b}$CHNH)$_n$: $C=O$, $R^{6b}$
- on (COCHNH)$_{x-y}$: $R^{5a}$, $C=O$, $R^{7a}$, $R^{8a}$
- on (COR$^{5b}$CHNH)$_y$: $C=O$, $R^{7b}$, $R^{8b}$ $$R^1-(OCH_2CH_2)_k-L^3-L^4-(NHCHCO)_{m-n}-(NHCHR^{4b}CO)_n-(NHCHCO)_{x-y}-(NHCHR^{5b}CO)_y-R^3 \quad (4)$$

with side chains:
- on (NHCHCO)$_{m-n}$: $R^{4a}$, $C=O$, $R^{6a}$
- on (NHCHR$^{4b}$CO)$_n$: $C=O$, $R^{6b}$
- on (NHCHCO)$_{x-y}$: $R^{5a}$, $C=O$, $R^{7a}$, $R^{8a}$
- on (NHCHR$^{5b}$CO)$_y$: $C=O$, $R^{7b}$, $R^{8b}$ wherein:

$R^1$ is a hydrogen atom or an unsubstituted or substituted linear or branched alkyl group having 1 to 12 carbon atoms;

$R^2$ is a hydrogen atom, an unsubstituted or substituted linear or branched alkyl group having 1 to 12 carbon atoms, or an unsubstituted or substituted linear or branched alkylcarbonyl group having 1 to 24 carbon atoms;

$R^3$ is a hydroxyl group, an unsubstituted or substituted linear or branched alkyloxy group having 1 to 12 carbon atoms, an unsubstituted or substituted linear or branched alkenyloxy group having 2 to 12 carbon atoms, an unsubstituted or substituted linear or branched alkynyloxy group having 2 to 12 carbon atoms, or an unsubstituted or substituted linear or branched alkyl-substituted imino group having 1 to 12 carbon atoms;

$R^{4a}$, $R^{4b}$, $R^{5a}$, and $R^{5b}$ are each independently a methylene group or an ethylene group;

$R^{6a}$ and $R^{6b}$ are each independently a group selected from following formulas (i) to (iv):

$$-NH-(CH_2)_{p1}-[NH-(CH_2)_{q1}-]_{r1}NH_2 \quad (i)$$

$$-NH-(CH_2)_{p2}-N[-(CH_2)_{q2}-NH_2]_2 \quad (ii)$$

$$-NH-(CH_2)_{p3}-N\{[-(CH_2)_{q3}-NH_2][-(CH_2)_{q4}-NH-]_{r2}H\} \quad (iii); \text{ and}$$

$$-NH-(CH_2)_{p4}-N\{-(CH_2)_{q5}-N[-(CH_2)_{q6}-NH_2]_2\}_2 \quad (iv),$$

where p1 to p4, q1 to q6, and r1 and r2 are each independently an integer of 1 to 5, $R^{7a}$ and $R^{7b}$ are each independently —O— or —NH—;

$R^{8a}$ and $R^{8b}$ are each independently a saturated or unsaturated linear or branched aliphatic hydrocarbon group having 6 to 27 carbon atoms, an aromatic hydrocarbon group having 6 to 27 carbon atoms, or a steryl group;

Q is —NH$_2$, —NHC(=NH)NH$_2$, or a group represented by the following formula (II):

$$\text{(II)} \quad \text{4-methylimidazole structure with HN- substituent}$$

$L^1$ and $L^3$ are each independently —S—S— or a valence bond;

$L^2$ is —NH—, —O—, —O(CH$_2$)$_{p1}$—NH—, or -L$^{2a}$-(CH$_2$)$_{q1}$-L$^{2b}$-, where p1 and q1 are each independently an integer of 1 to 5, L$^{2a}$ is OCO, OCONH, NHCO, NHCOO, NHCONH, CONH, or COO, and L$^{2b}$ is NH or O;

$L^4$ is —OCO—(CH$_2$)$_{p2}$—CO—, —NHCO—(CH$_2$)$_{p3}$—CO—, or -L$^{4a}$-(CH$_2$)$_{q2}$—CO—, where p2, p3, and q2 are each independently an integer of 1 to 5, L$^{4a}$ is OCONH, —CH$_2$NHCO—, NHCOO, NHCONH, CONH, or COO;

k is an integer of 30 to 20,000;
s is an integer of 1 to 6;
m is an integer of 1 to 300;
n is an integer of 0 to m;
x is an integer of 0 to 80;
y is an integer of 0 to x;
z is an integer of 2 to 300;

the total number of primary amino groups and secondary amino groups included in all Q's is defined as w, the total number of primary amino groups and secondary amino groups included in (m-n) of group $R^{6a}$ and n of group $R^{6b}$ is also defined as w, and at least one, but less than w of, hydrogen atom(s) of said primary and secondary amino groups is (are) substituted with (an) acyl group(s) having the substituted phenylboronic acid group, with the proviso that the binding order of the amino acid residue(s) having the cationic side chain(s), the amino acid residue(s) containing the substituted phenylboronic acid group(s), and if present the amino acid residue(s) containing a hydrophobic side chain, is arbitrary.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: sense strand of siRNA for human vascular
      endothelial growth factor including dT terminus

<400> SEQUENCE: 1
gaucucauca ggguacucct t                                              21

<210> SEQ ID NO 2
<211> LENGTH: 21
<212> TYPE: DNA
<213> ORGANISM: Artificial Sequence
<220> FEATURE:
<223> OTHER INFORMATION: antisense strand of siRNA for human vascular
      endothelial growth factor including dT terminus

<400> SEQUENCE: 2
ggaguacccu gaugagauct t                                              21

<210> SEQ ID NO 3
<211> LENGTH: 21
<212> TYPE: RNA
<213> ORGANISM: Artificial Sequence
<220> FEATURE:
<223> OTHER INFORMATION: sense strand of non-therapeutic siRNA

<400> SEQUENCE: 3
uucuccgaac gugucacguu u                                              21

<210> SEQ ID NO 4
```

```
<211> LENGTH: 21
<212> TYPE: RNA
<213> ORGANISM: Artificial Sequence
<220> FEATURE:
<223> OTHER INFORMATION: antisense strand of non-therapeutic siRNA

<400> SEQUENCE: 4
acgugacacg uucggagaau u                                              21

<210> SEQ ID NO 5
<211> LENGTH: 21
<212> TYPE: RNA
<213> ORGANISM: Artificial Sequence
<220> FEATURE:
<223> OTHER INFORMATION: sense strand of siRNA for firefly luciferase

<400> SEQUENCE: 5
cuuacgcuga cuacuucgau u                                              21

<210> SEQ ID NO 6
<211> LENGTH: 21
<212> TYPE: RNA
<213> ORGANISM: Artificial Sequence
<220> FEATURE:
<223> OTHER INFORMATION: antisense strand of siRNA for firefly
      luciferase

<400> SEQUENCE: 6
ucgaaguacu cagcguaagu u                                              21
```